US009367013B2

(12) United States Patent
Morita et al.

(10) Patent No.: US 9,367,013 B2
(45) Date of Patent: Jun. 14, 2016

(54) IMAGING DEVICE, IMAGE FORMING APPARATUS, AND CONTAMINATION INSPECTION METHOD

(71) Applicants: Kenji Morita, Tokyo (JP); Nobuyuki Satoh, Kanagawa (JP); Mamoru Yorimoto, Kanagawa (JP); Masayuki Fujii, Kanagawa (JP); Daisaku Horikawa, Kanagawa (JP); Suguru Yokozawa, Kanagawa (JP); Masahiro Hiranuma, Kanagawa (JP); Masaya Kawarada, Kanagawa (JP)

(72) Inventors: Kenji Morita, Tokyo (JP); Nobuyuki Satoh, Kanagawa (JP); Mamoru Yorimoto, Kanagawa (JP); Masayuki Fujii, Kanagawa (JP); Daisaku Horikawa, Kanagawa (JP); Suguru Yokozawa, Kanagawa (JP); Masahiro Hiranuma, Kanagawa (JP); Masaya Kawarada, Kanagawa (JP)

(73) Assignee: RICOH COMPANY, LTD., Tokyo (JP)

(*) Notice: Subject to any disclaimer, the term of this patent is extended or adjusted under 35 U.S.C. 154(b) by 0 days.

(21) Appl. No.: 14/789,015

(22) Filed: Jul. 1, 2015

(65) Prior Publication Data
US 2016/0004202 A1    Jan. 7, 2016

(30) Foreign Application Priority Data

Jul. 2, 2014    (JP) ................................. 2014-137121
May 22, 2015   (JP) ................................. 2015-104651

(51) Int. Cl.
*B41J 2/01* (2006.01)
*G03G 15/00* (2006.01)
(Continued)

(52) U.S. Cl.
CPC . *G03G 15/55* (2013.01); *B41J 2/01* (2013.01); *G01J 3/46* (2013.01); *G01J 3/501* (2013.01);
(Continued)

(58) Field of Classification Search
CPC . H04N 1/4433; H04N 1/4097; H04N 1/6033; H04N 1/6044; H04N 1/6055; H04N 1/6086; G01N 21/251; G01N 15/0205; G06K 15/027; G06K 15/028; G06K 15/029; G01J 3/46; G01J 3/501; G03J 15/55; G03G 15/5062
USPC .............. 347/19; 358/1.9, 2.1, 504, 509, 518, 358/520, 521; 382/100, 141, 162, 167, 274; 356/401
See application file for complete search history.

(56) References Cited

U.S. PATENT DOCUMENTS 8,514,396 B2 *  8/2013  Satoh .................... G01J 3/0248
                                                       356/402
8,902,466 B2    12/2014  Satoh
(Continued)

FOREIGN PATENT DOCUMENTS

JP    2003-232746    8/2003
JP    2004-228654    8/2004
(Continued)

OTHER PUBLICATIONS
U.S. Appl. No. 14/565,182, filed Dec. 9, 2014.

*Primary Examiner* — Anh T. N. Vo
(74) *Attorney, Agent, or Firm* — Oblon, McClelland, Maier & Neustadt, L.L.P.

(57) ABSTRACT

An imaging device includes: a housing having an opening in a surface thereof facing a subject; a light source that irradiates the subject with light; a two-dimensional image sensor that captures, from inside of the housing through the opening; an image of the subject illuminated by the light source; an optical member that is disposed between the two-dimensional image sensor and the opening and that transmits light reflected off the subject; and a contamination inspection member that is disposed between the opening and the optical member and that causes inspection light for inspecting contamination on the optical member to be incident upon the two-dimensional image sensor via the optical member.

12 Claims, 16 Drawing Sheets

(51) Int. Cl.
   *G01N 21/25* (2006.01)
   *H04N 1/60* (2006.01)
   *G01N 15/02* (2006.01)
   *G01J 3/46* (2006.01)
   *G01J 3/50* (2006.01)

(52) U.S. Cl.
   CPC .......... *G01N 15/0205* (2013.01); *G01N 21/251* (2013.01); *G03G 15/5062* (2013.01); *H04N 1/6086* (2013.01)

(56) References Cited

U.S. PATENT DOCUMENTS

| | | | |
|---|---|---|---|
| 8,922,831 B2 * | 12/2014 | Suzuki | G06K 15/027 358/1.9 |
| 8,947,731 B2 | 2/2015 | Suzuki et al. | |
| 2012/0069411 A1 | 3/2012 | Satoh et al. | |
| 2012/0236308 A1 | 9/2012 | Satoh | |
| 2013/0027720 A1 | 1/2013 | Satoh | |
| 2013/0027721 A1 | 1/2013 | Kobayashi et al. | |
| 2013/0135484 A1 | 5/2013 | Satoh et al. | |
| 2013/0208289 A1 | 8/2013 | Satoh et al. | |
| 2013/0229671 A1 | 9/2013 | Yokozawa et al. | |
| 2013/0242319 A1 | 9/2013 | Suzuki et al. | |
| 2013/0242320 A1 | 9/2013 | Suzuki et al. | |
| 2013/0242321 A1 | 9/2013 | Okada et al. | |
| 2013/0242361 A1 | 9/2013 | Matsumoto et al. | |
| 2013/0258368 A1 | 10/2013 | Shigemoto et al. | |
| 2013/0258369 A1 | 10/2013 | Suzuki et al. | |
| 2015/0070737 A1 | 3/2015 | Hirata et al. | |
| 2015/0146053 A1 | 5/2015 | Satoh et al. | |
| 2015/0158309 A1 | 6/2015 | Fujii et al. | |
| 2015/0162372 A1 | 6/2015 | Yorimoto et al. | |

FOREIGN PATENT DOCUMENTS

| | | |
|---|---|---|
| JP | 2013-051671 | 3/2013 |
| JP | 2013-207595 | 10/2013 |
| JP | 2013-217905 | 10/2013 |

* cited by examiner

IMAGING DEVICE, IMAGE FORMING APPARATUS, AND CONTAMINATION INSPECTION METHOD

CROSS-REFERENCE TO RELATED APPLICATIONS

The present application claims priority to and incorporates by reference the entire contents of Japanese Patent Application No. 2014-137121 filed in Japan on Jul. 2, 2014 and Japanese Patent Application No. 2015-104651 filed in Japan on May 22, 2015.

BACKGROUND OF THE INVENTION

1. Field of the Invention

The present invention relates to an imaging device, an image forming apparatus, and a contamination inspection method.

2. Description of the Related Art

An imaging device is known that performs colorimetry for a pattern formed by an image forming apparatus on a recording medium using a coloring material such as ink, by capturing an image of the pattern using a two-dimensional image sensor and converting an RGB value of the pattern thus obtained into a color specification value in a standard color space (see, for example, Japanese Patent Application Laid-open No. 2013-207595).

The imaging device disclosed in Japanese Patent Application Laid-open No. 2013-207595 includes a transparent optical member (a mist blocking transparent member) to block an opening in a housing in which the two-dimensional image sensor is disposed, thereby preventing mist-like ink produced during the formation of the pattern from entering inside the housing. In order to detect contamination on the mist blocking transparent member, the imaging device disclosed in Japanese Patent Application Laid-open No. 2013-207595 captures two images with different distances between the recording medium and the housing and determines whether or not the mist blocking transparent member is contaminated on the basis of a difference in a contaminated pixel detected from the two images.

To inspect whether the mist blocking transparent member is contaminated, however, the imaging device disclosed in Japanese Patent Application Laid-open No. 2013-207595 is required to analyze the two images captured by changing the distance between the recording medium and the housing. A need thus exists for more convenient inspection of contamination on the optical member.

SUMMARY OF THE INVENTION

It is an object of the present invention to at least partially solve the problems in the conventional technology.

According to the present invention, there is provided an imaging device comprising: a housing having an opening in a surface thereof facing a subject; a light source that irradiates the subject with light; a two-dimensional image sensor that captures, from inside of the housing through the opening, an image of the subject illuminated by the light source; an optical member that is disposed between the two-dimensional image sensor and the opening and that transmits light reflected off the subject; and a contamination inspection member that is disposed between the opening and the optical member and that causes inspection light for inspecting contamination on the optical member to be incident upon the two-dimensional image sensor via the optical member.

The present invention also provides an image forming apparatus comprising the above-described imaging device.

The present invention also provides a contamination inspection method executed by an imaging device that comprises: a housing having an opening in a surface thereof facing a subject; a light source that irradiates the subject with light; a two-dimensional image sensor that captures, from inside of the housing through the opening, an image of the subject illuminated by the light source; and an optical member that is disposed between the two-dimensional image sensor and the opening and that transmits light reflected off the subject, the contamination inspection method comprising: causing, by a contamination inspection member disposed between the opening and the optical member, inspection light for inspecting contamination on the optical member to be incident upon the two-dimensional image sensor via the optical member; imaging, by the two-dimensional image sensor, the inspection light; and determining, by a determining unit, whether or not the optical member is contaminated using an inspection image obtained through the imaging of the inspection light by the two-dimensional image sensor.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

The following describes in detail an imaging device, an image forming apparatus, and a contamination inspection method according to an example embodiment of the present invention with reference to the accompanying drawings. While the embodiment to be described hereunder is exemplified by an ink jet printer as an example of the image forming apparatus to which the present invention is applied, the present invention is widely applicable to various types of image forming apparatuses that form an image on a recording medium.

Mechanical Configuration of Image Forming Apparatus

Figure 1:
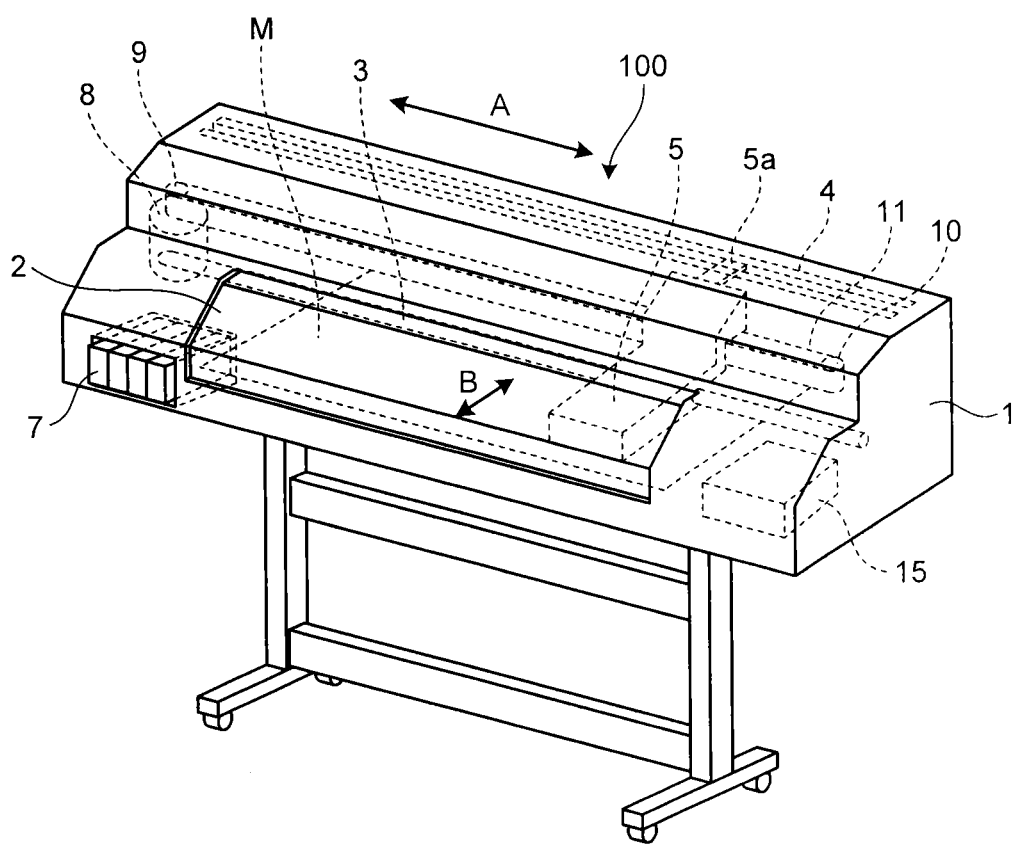
FIG. 1 is a perspective view illustrating the inside of an image forming apparatus of an embodiment of the present invention.
Figure 2:
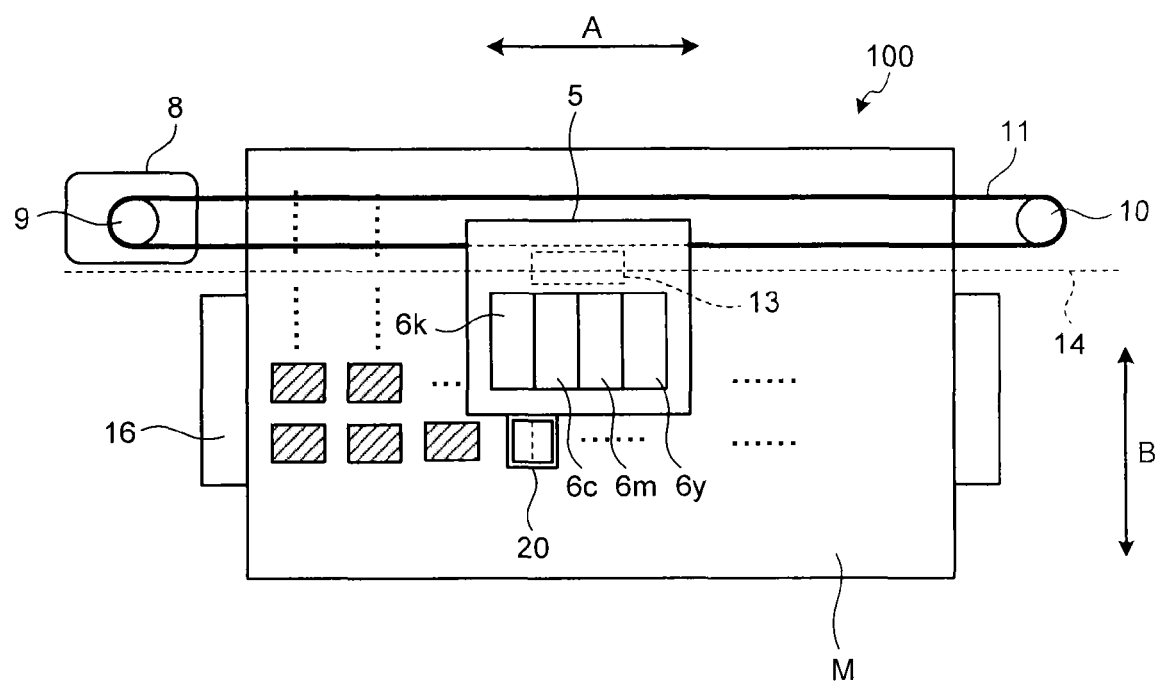
FIG. 2 is a top view illustrating a mechanical configuration of the inside of the image forming apparatus.

The following describes a mechanical configuration of an image forming apparatus 100 according to the present embodiment with reference to FIGS. 1 and 2. FIG. 1 is a perspective view illustrating the inside of the image forming apparatus 100. FIG. 2 is a top view illustrating a mechanical configuration of the inside of the image forming apparatus 100.

As illustrated in FIG. 1, the image forming apparatus 100 in the present embodiment includes a carriage 5 that reciprocates in a main-scanning direction (in the direction indicated by the arrow A in FIG. 1). The carriage 5 is supported by a main guide rod 3 that extends along the main-scanning direction. The carriage 5 includes a connecting tab 5a. The connecting tab 5a engages a sub-guide member 4 disposed in parallel with the main guide red 3 to thereby stabilize posture of the carriage 5.

As illustrated in FIG. 2, the carriage 5 includes, for example, four recording heads 6y, 6m, 6c, and 6k mounted thereon. The recording head 6y ejects yellow ink. The recording head 6m ejects magenta ink. The recording head 6c ejects cyan ink. The recording head 6k ejects black ink. The recording heads 6y, 6m, 6c, and 6k will hereinafter be referred to collectively as a recording head 6. The recording head 6 is supported by the carriage 5 such that an ink ejecting surface faces downward (the side of a recording medium M).

A cartridge 7 that serves an ink supply unit supplying ink to the recording head 6 is not mounted on the carriage 5 and disposed at a predetermined position within the image forming apparatus 100. The cartridge 7 is connected with the recording head 6 through a pipe not illustrated and ink is supplied from the cartridge 7 to the recording head 6 through the pipe.

The carriage 5 is coupled to a timing belt 11 stretched across a driving pulley 9 and a driven pulley 10. The driving pulley 9 is rotated through driving of a main-scanning motor 8. The driven pulley 10 includes a mechanism that adjusts a distance from the driving pulley 9 and functions to give predetermined tension to the timing belt 11. The carriage 5 reciprocates in the main-scanning direction as the timing belt 11 is fed by the driving of the main-scanning motor 8. As illustrated in FIG. 2, for example, the movement of the carriage 5 in the main-scanning direction is controlled on the basis of an encoder value obtained through detection of a mark of an encoder sheet 14 by an encoder sensor 13 disposed in the carriage 5.

The image forming apparatus 100 in the present embodiment further includes a maintenance mechanism 15 for maintaining reliability of the recording head 6. The maintenance mechanism 15, for example, cleans and caps the ink ejecting surface of the recording head 6 and discharges unnecessary ink from the recording head 6.

As illustrated in FIG. 2, a platen 16 is disposed at a position opposed to the ejecting surface of the recording head 6. The platen 16 supports the recording medium M when ink is ejected from the recording head 6 onto the recording medium M. The image forming apparatus 100 according to the present embodiment is so wide that the carriage 5 moves a long distance in the main-scanning direction. Thus, the platen 16 is configured such that a plurality of plate-shaped members are connected to each other in the main-scanning direction (in the moving direction of the carriage 5). The recording medium M is pinched between conveying rollers that is driven by a sub-scanning motor not illustrated and intermittently conveyed along the platen 16 in a sub-scanning direction (a direction orthogonal to the main-scanning direction) indicated by the arrow B in FIG. 2.

As the carriage 5 reciprocates in the main-scanning direction (in the direction indicated by the arrow A in FIG. 2), the recording head 6 moves in the main-scanning direction relative to the recording medium M on the platen 16. In this process, the recording head 6 ejects ink from a nozzle surface to the recording medium M to thereby form an image on the recording medium M.

Each of the above-described components that constitute the image forming apparatus 100 according to the present embodiment is disposed inside an outer housing 1. A covering member 2 is openably disposed in the outer housing 1. When the image forming apparatus 100 is to be serviced or a paper jam occurs, the covering member 2 may be opened to thereby allow a service job to be performed for each of the components disposed inside the outer housing 1.

At a time of color adjustment for making color adjustments, the image forming apparatus 100 in the present embodiment causes the recording head 6 to eject ink onto the recording medium M on the platen 16 to thereby form a large number of colorimetric patterns. The image forming apparatus 100 thereby performs colorimetry for the colorimetric patterns. The colorimetric patterns are formed on the recording medium M through an actual use of ink by the image forming apparatus 100, thus representing characteristics unique to the image forming apparatus 100. Accordingly, a device profile that describes the characteristics unique to the image forming apparatus 100 can be generated or corrected using colorimetric values of the large number of colorimetric patterns. By performing color conversion between the standard color space and device-dependent colors on the basis of this device profile, the image forming apparatus 100 can output an image with high reproducibility.

The image forming apparatus 100 in the present embodiment includes a colorimetric camera 20 that has a function of calculating a colorimetric value by capturing an image of the colorimetric pattern formed on the recording medium M. As illustrated in FIG. 2, the colorimetric camera 20 is supported by the carriage 5 on which the recording head 6 is mounted. The calorimetric camera 20 moves over the recording medium M, on which the colorimetric pattern is formed, through conveyance of the recording medium M and movement of the carriage 5 and, on reaching a position that faces the colorimetric pattern, captures the image of the colorimetric pattern. The colorimetric camera 20 calculates the calorimetric value of the colorimetric pattern in accordance with an RGB value of the colorimetric pattern obtained through the image capturing.

Specific Example of Colorimetric Camera

Figure 3A:
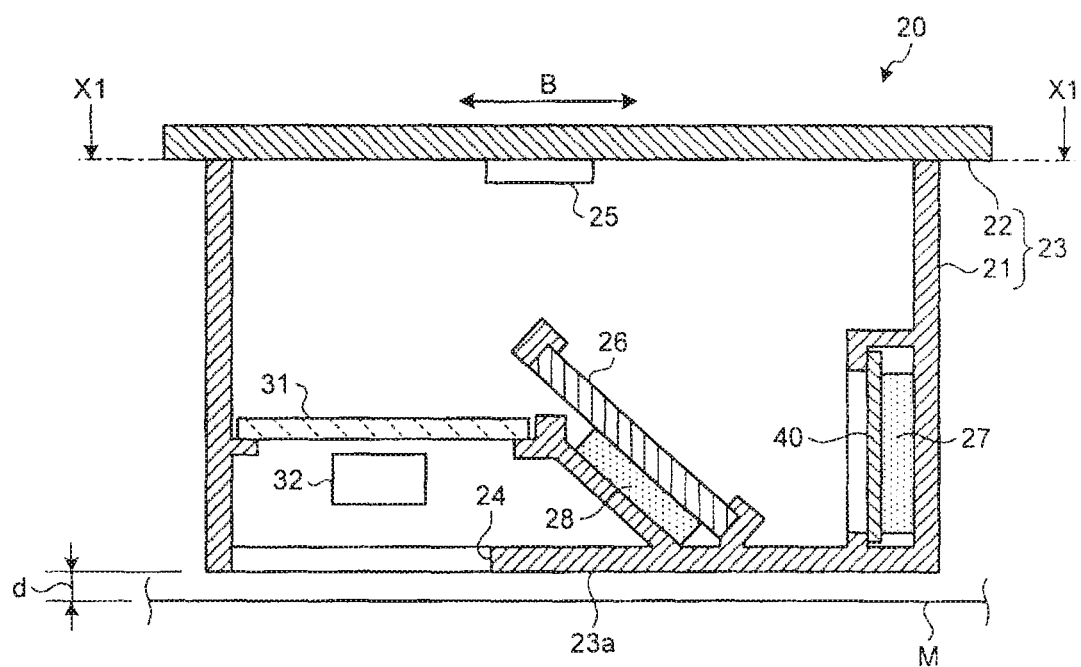
FIG. 3A is a longitudinal sectional view illustrating a colorimetric camera.
Figure 3B:
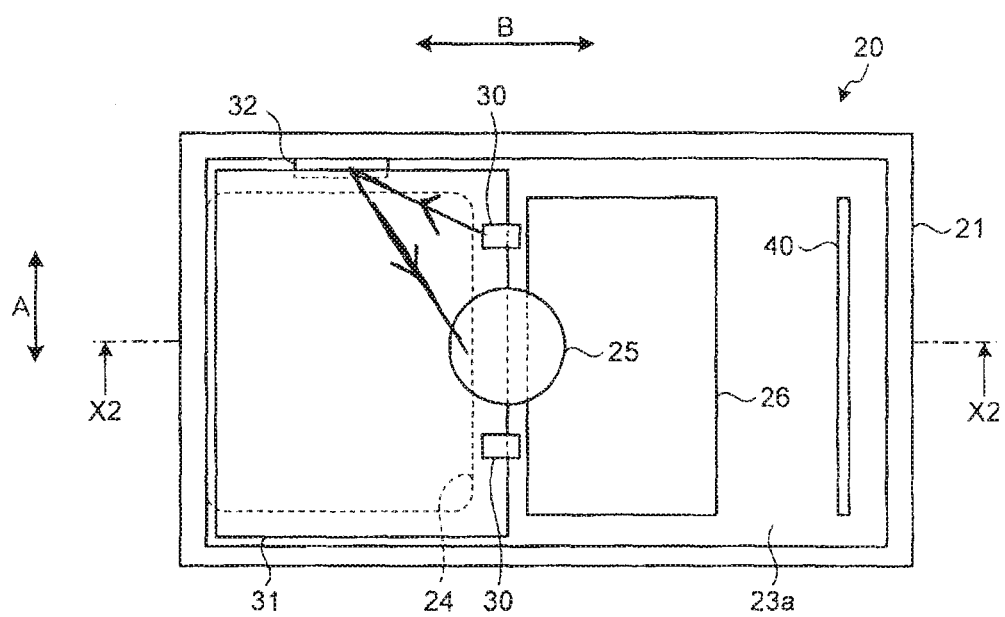
FIG. 3B is a plan view illustrating the inside of the colorimetric camera as viewed from the X1 direction in FIG. 3A.

The following describes with reference to FIGS. 3A and 3B a specific example of the colorimetric camera 20. FIGS. 3A and 3B illustrate an exemplary mechanical configuration of the colorimetric camera 20. FIG. 3A is a longitudinal sectional view illustrating the colorimetric camera 20 (a sectional view taken along line X2-X2 in FIG. 3B). FIG. 3B is a plan view illustrating the inside of the colorimetric camera 20 as viewed from the X1 direction in FIG. 3A. It is noted that, to illustrate positional relations among different members disposed inside the colorimetric camera 20, FIG. 3B omits illustrating structural members and related parts that support these members.

The colorimetric camera 20 includes a housing 23 that is composed of a frame 21 and a substrate 22. The frame 21 is formed into a closed-bottom cylinder having an open first end that assumes an upper surface of the housing 23. The substrate 22 is fastened to, and integrated with, the frame 21 so as to close the open end of the frame 21 to thereby constitute the upper surface of the housing 23.

The housing 23 is fixed to the carriage 5 such that a bottom surface 23a thereof faces the recording medium M on the platen 16 with a predetermined distance d therebetween. The bottom surface 23a of the housing 23 that faces the recording medium M has an opening 24 that allows the image of the colorimetric pattern (subject) formed on the recording medium M to be captured from the inside of the housing 23.

A two-dimensional image sensor 25 that captures an image is disposed inside the housing 23. The two-dimensional image sensor 25 includes an imaging element, such as a CCD sensor and a CMOS sensor, an image forming lens, and the like. The two-dimensional image sensor 25 is mounted on, for example, an inner surface (a component mounting surface) of the substrate 22 such that a light-receiving surface faces the bottom surface 23a of the housing 23.

Additionally, a reference chart 40 and a reflecting mirror 26 are disposed inside the housing 23. During the performance of colorimetry for the colorimetric patterns, the two-dimensional image sensor 25 captures an image of the reference chart 40 together with the images of the colorimetric patterns. The reflecting mirror 26 guides an optical image of the reference chart 40 onto the two-dimensional image sensor 25. The reference chart 40 is pressed against a structural member by, for example, compression resilience of a cushioning member 27 and is fixed in a condition of extending in parallel with a side surface of the frame 21. The reflecting mirror 26 is pressed against a structural member by, for example, compression resilience of a cushioning member 28 and is fixed in a condition of being inclined at a predetermined angle with respect to the bottom surface 23a of the housing 23. The reference chart 40 will be described in detail later.

In addition, illumination light sources 30 are disposed inside the housing 23 (see FIG. 3B). The illumination light sources 30 substantially uniformly illuminate an imaging area of the two-dimensional image sensor 25 during the performance of colorimetry for the colorimetric patterns. A light emitting diode (LED), for example, is used as the illumination light sources 30. In the present embodiment, two LEDs are used for the illumination light sources 30. The LEDs used for the illumination light sources 30 are mounted, for example, on the inner surface of the substrate 22. It should, however, be noted that the illumination light sources 30 are required only to be configured so as to be capable of illuminating the imaging area of the two-dimensional image sensor 25 substantially uniformly and are not necessarily required to be directly mounted on the substrate 22. Additionally, while the LEDs are used for the illumination light sources 30 in the present embodiment, the type of light sources is not limited to the LED. An organic EL may, for example, be used for the illumination light sources 30. When the organic EL is used for the illumination light sources 30, illumination light close to a spectral distribution of sunlight can be obtained, so that colorimetric accuracy can be expected to be improved.

A covering member 31 is additionally disposed inside the housing 23. The covering member 31 prevents ink mist or the like that enters the housing 23 through the opening 24 from sticking to, for example, the two-dimensional image sensor 25, the illumination light sources 30, and the reference chart 40. As described earlier, the image forming apparatus 100 in the present embodiment is configured such that ink is ejected from the nozzle surface of the recording head 6 mounted on the carriage 5 toward the recording medium M to thereby form an image on the recording medium M. The colorimetric camera 20 in the present embodiment is supported by the carriage 5 such that the opening 24 in the housing 23 faces the recording medium M. As a result, the ink mist that represents mist-like minute ink particles generated during image formation enters the housing 23 of the colorimetric camera 20 through the opening 24, so that the ink mist may stick to, for example, the two-dimensional image sensor 25, the illumination light sources 30, and the reference chart 40. The two-dimensional image sensor 25, the illumination light sources 30, or the reference chart 40 contaminated with the ink mist prevents a correct RGB value from being obtained during the performance of colorimetry for the colorimetric patterns.

The colorimetric camera 20 in the present embodiment thus includes the covering member 31 in the housing 23 to thereby prevent the ink mist generated during the image formation from sticking to, for example, the two-dimensional image sensor 25, the illumination light sources 30, and the reference chart 40. The covering member 31 also has a function of preventing, for example, outside dust and dirt, in addition to the ink mist, from entering the housing 23. The covering member 31 is a transparent optical member having a sufficient transmissivity to light from the illumination light sources 30. The covering member 31 is disposed, as illustrated in FIG. 3A, for example, to extend substantially in parallel with the opening 24 in an optical path between the two-dimensional image sensor 25 and the opening 24. It is noted that FIG. 3A illustrates only an exemplary disposition of the covering member 31 and the covering member 31 is required only to at least be disposed between the two-dimensional image sensor 25 and the opening 24.

A reference member 32 is disposed between the opening 24 in the housing 23 and the covering member 31. The reference member 32 represents an exemplary contamination inspection member that causes inspection light for inspecting contamination on the covering member 31 to be incident upon the two-dimensional image sensor 25 via the covering member 31. For example, the reference member 32 is formed into a thin plate having an even white surface and serves as a reflecting member, diffusing and reflecting light from the illumination light sources 30 on its white surface and causing the resultant light to be incident upon the two-dimensional image sensor 25 as the inspection light. The present embodiment will be described for a case in which the reference member 32 has a white surface. The reference member 32 may nonetheless have any color other than white when the color is identifiable from the ink mist sticking to the covering member 31 as will be described later.

Preferably, the reference member 32 is disposed at position outside an optical path of the light that is reflected off the colorimetric patterns and is incident upon the two-dimensional image sensor 25 through the opening 24 when the two-dimensional image sensor 25 captures images of the colorimetric patterns illuminated with the illumination light sources 30. As illustrated in FIGS. 3A and 3B, for example, the reference member 32 is bonded to an inner wall of the housing 23 between the opening 24 and the covering member 31, having a surface opposite to the white surface as a bonding surface. This arrangement can effectively prevent inconvenience of fluctuating RGB values of the colorimetric patterns as affected by the diffused and reflected light at the reference member 32 during the performance of colorimetry for the colorimetric patterns. It is noted that the reference member 32 is required only to be disposed at a position outside the optical path of the light that is reflected off the colorimetric patterns and is incident upon the two-dimensional image sensor 25 and the reference member 32 does not necessarily have to be bonded to the inner wall of the housing 23.

Specific Example of Reference Chart

Figure 4:
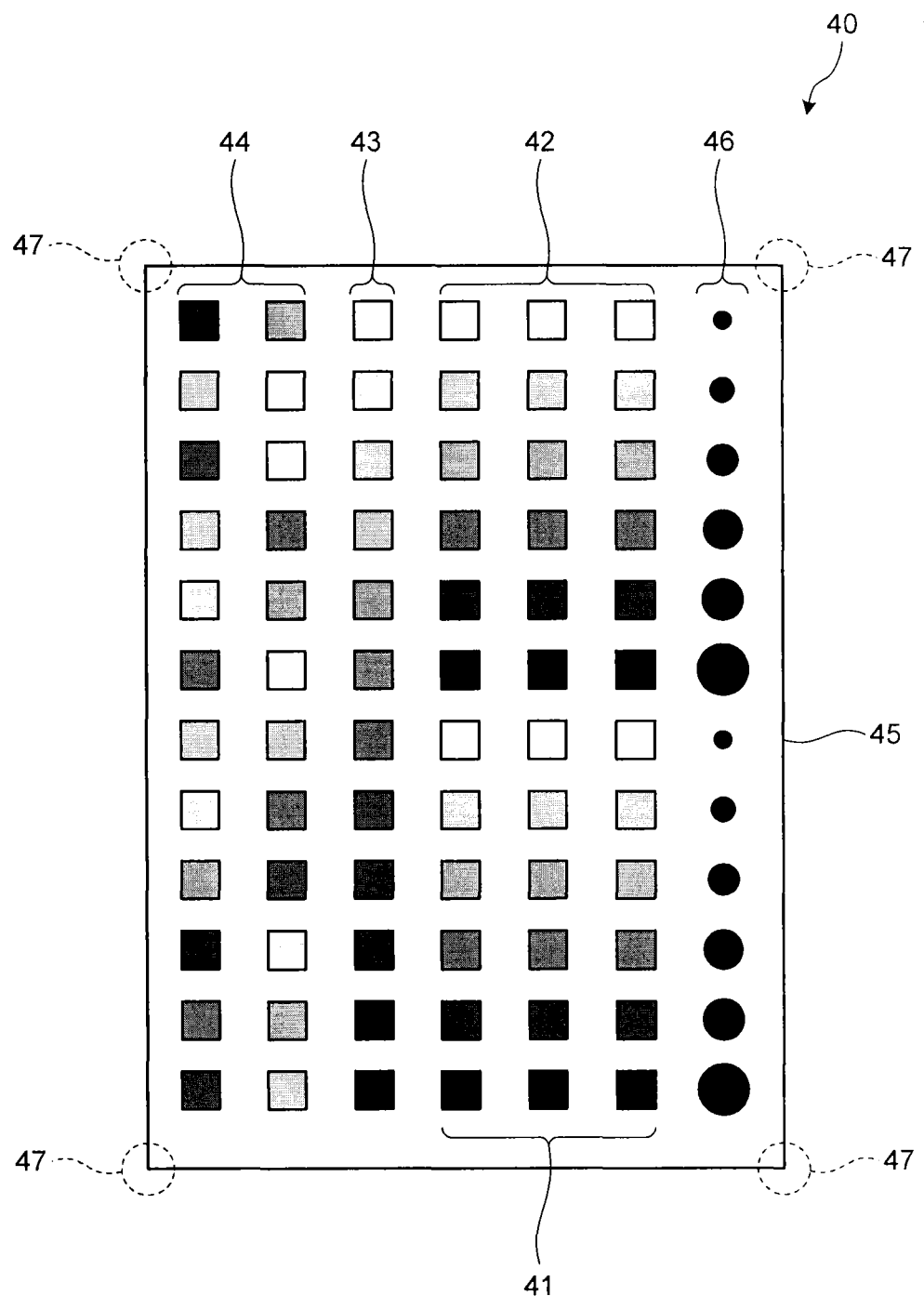
FIG. 4 is a diagram illustrating a specific example of a reference chart.

The following describes in detail with reference to FIG. 4 the reference chart 40 disposed inside the housing 23 of the colorimetric camera 20. FIG. 4 is a diagram illustrating a specific example of the reference chart 40.

The reference chart 40 illustrated in FIG. 4 includes a plurality of reference patch rows 41 to 44 in which colorimetric reference patches are arrayed, a dot diameter measuring pattern row 46, a distance measuring line 45, and chart position identifying makers 47.

The reference patch rows 41 to 44 include reference patch rows 41 in which reference patches of primary colors of YMCK are arrayed in order of gradation, reference patch rows 42 in which reference patches of secondary colors of RGB are arrayed in order of gradation, a reference patch row 43 in which gray scale reference patches are arrayed in order of gradation, and reference patch rows 44 in which reference patches of tertiary colors are arrayed. The dot diameter measuring pattern row 46 is a pattern row for geometric shape measurement in which circular patterns having different sizes are arrayed in order of size and can be used for measurement of a dot diameter of an image formed on the recording medium M.

The distance measuring line 45 is formed as a rectangular frame that surrounds the reference patch rows 41 to 44 and the dot diameter measuring pattern row 46. The chart position identifying makers 47 are disposed at four corners of the distance measuring line 45 and functions as markers for identifying the position of each reference patch. The position of the reference chart 40 and the position of each reference patch or pattern can be identified by identifying, from the image of the reference chart 40 captured by the two-dimensional image sensor 25, the distance measuring line 45 and the chart position identifying makers 47 at the four corners thereof.

Each of the reference patches that constitute the colorimetric reference patch rows 41 to 44 is used as a reference for a color tone in which an imaging condition of the colorimetric camera 20 is incorporated. It is noted that the configuration of the colorimetric reference patch rows 41 to 44 arrayed on the reference chart 40 is not limited to the example illustrated in FIG. 4 and any reference patch rows may be applied. For example, a reference patch that can identify as wide a color range as possible may be used. Alternatively, the reference patch rows 41 in which reference patches of primary colors of YMCK are arrayed or the reference patch row 43 in which gray scale reference patches are arrayed may be configured to include patches of colorimetric values of ink used in the image forming apparatus 100. Still alternatively, the reference patch rows 42 in which reference patches of secondary colors of RGB are arrayed may be configured to include patches of colorimetric values of colors to be produced by the ink used in the image forming apparatus 100, or may use a color chart that establishes colorimetric values, such as Japan Color.

While the reference chart 40 including the reference patch rows 41 to 44 having a common patch (color chart) form is used in the present embodiment, the reference chart 40 does not necessarily have to be configured to include such reference patch rows 41 to 44. The reference chart 40 is required only to be configured to include a plurality of colors usable in colorimetry arrayed such that their respective positions are identifiable.

When performing colorimetry for the colorimetric patterns, the colorimetric camera 20 in the present embodiment causes the two-dimensional image sensor 25 to simultaneously capture images of the colorimetric patterns formed on the recording medium M and of the reference chart 40 inside the housing 23 under illumination by the illumination light sources 30. The colorimetric camera 20 then calculates a colorimetric value of the colorimetric patterns using the images thus obtained. At this time, the position and angle of the reflecting mirror 26 are adjusted so that both the colorimetric patterns outside the housing 23 and the reference chart 40 inside the housing 23 can be brought into focus. "Simultaneously capturing the images", as used herein, refers to acquiring image data of one frame that includes both the colorimetric patterns and the reference chart 40. Specifically, when image data that includes both the colorimetric patterns and the reference chart 40 within a single frame is acquired even with a time difference involved in acquiring data for each pixel, the images of the colorimetric patterns and the reference chart 40 are simultaneously captured.

The mechanical configuration of the colorimetric camera 20 described above is a mere example and is not the only possible arrangement. The colorimetric camera 20 according to the present embodiment is required to be configured so as to be at least capable of performing colorimetry for the colorimetric patterns using the two-dimensional image sensor 25 and any change or modification can be appropriately made to the above-described configuration.

General Configuration of Control Mechanism of Image Forming Apparatus

Figure 5:
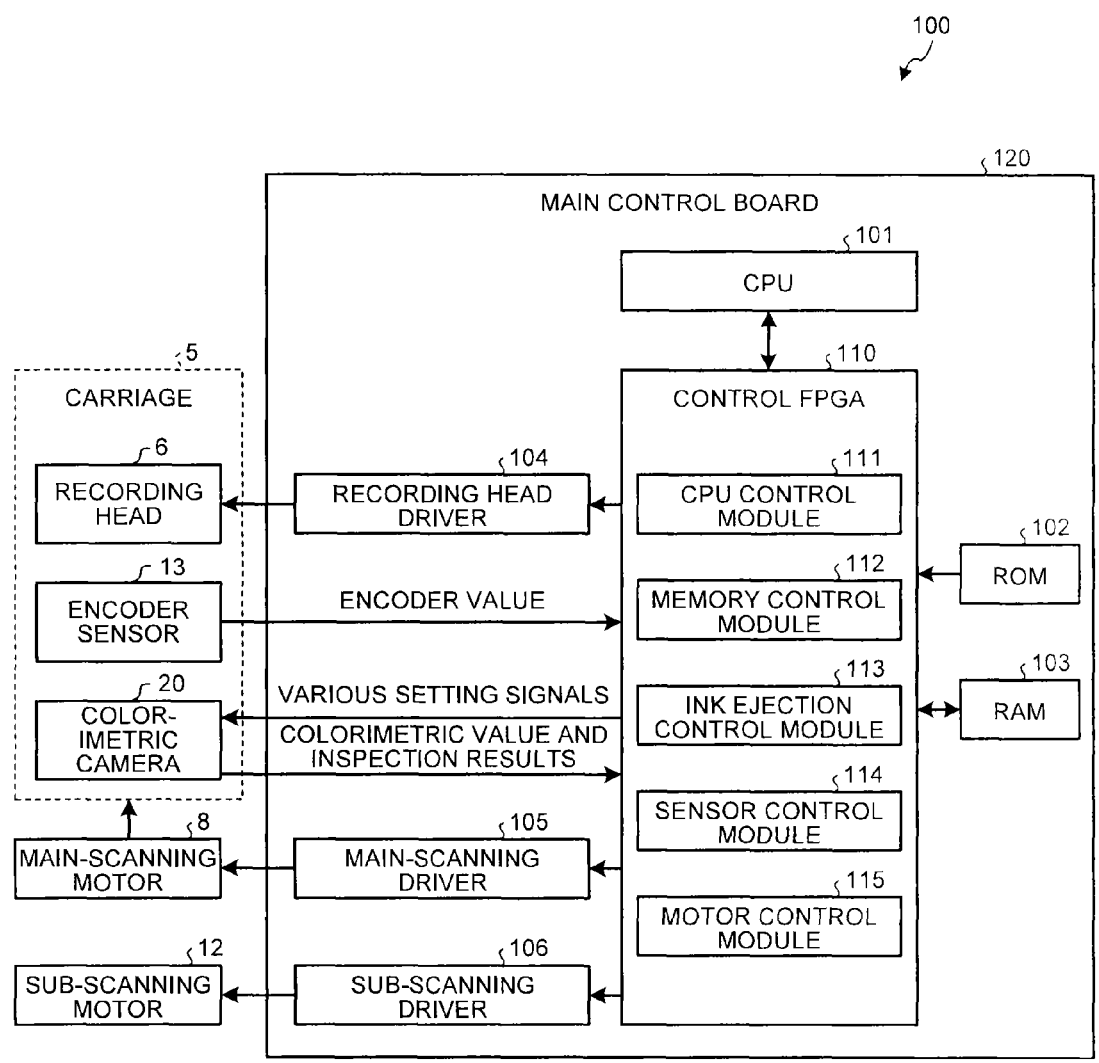
FIG. 5 is a block diagram illustrating a general configuration of a control mechanism of an image forming apparatus.

The following describes with reference to FIG. 5 a general configuration of a control mechanism of the image forming apparatus 100 according to the present embodiment. FIG. 5 is a block diagram illustrating the general configuration of the control mechanism of the image forming apparatus 100.

As illustrated in FIG. 5, the image forming apparatus 100 in the present embodiment includes a CPU 101, a ROM 102, a RAM 103, a recording head driver 104, a main-scanning driver 105, a sub-scanning driver 106, a control field-programmable gate array (FPGA) 110, the recording head 6, the colorimetric camera 20, the encoder sensor 13, the main-scanning motor 8, and a sub-scanning motor 12. The CPU 101, the ROM 102, the RAM 103, the recording head driver 104, the main-scanning driver 105, the sub-scanning driver 106, and the control FPGA 110 are mounted on a main control board 120. The recording head 6, the encoder sensor 13, and the colorimetric camera 20 are mounted on the carriage 5 as described earlier.

The CPU 101 provides general control for the image forming apparatus 100. For example, the CPU 101 uses the RAM 103 as a work area and executes various control programs stored in the ROM 102, thereby outputting control commands for controlling various types of operations performed in the image forming apparatus 100.

The recording head driver 104, the main-scanning driver 105, and the sub-scanning driver 106 drive the recording head 6, the main-scanning motor 8, and the sub-scanning motor 12, respectively.

The control FPGA 110 cooperates with the CPU 101 to control various types of operations in the image forming apparatus 100. The control FPGA 110 includes, as functional elements, a CPU control module 111, a memory control module 112, an ink ejection control module 113, a sensor control module 114, and a motor control module 115, for example.

The CPU control module 111 communicates with the CPU 101 to thereby transmit various types of information acquired by the control FPGA 110 to the CPU 101 and input control commands output from the CPU 101.

The memory control module 112 provides memory control for the CPU 101 to access the ROM 102 or the RAM 103.

The ink ejection control module 113 controls operations of the recording head driver 104 in accordance with the control command from the CPU 101 to thereby control timing at which ink is to be ejected from the recording head 6 that is driven by the recording head driver 104.

The sensor control module 114 performs processing for a sensor signal, such as an encode value output from the encoder sensor 13.

The motor control module 115 controls operations of the main-scanning driver 105 in accordance with the control command from the CPU 101, thereby controlling the main-scanning motor 8 driven by the main-scanning driver 105 to control movement of the carriage 5 in the main-scanning direction. The motor control module 115 further controls operations of the sub-scanning driver 106 in accordance with the control command from the CPU 101, thereby controlling the sub-scanning motor 12 driven by the sub-scanning driver 106 to control movement of the recording medium M on the platen 16 in the sub-scanning direction.

Each of the above-described modules represents an exemplary control function achieved by the control FPGA 110 and may be configured otherwise to achieve various other control functions achieved by the control FPGA 110. Additionally, all or part of the above-described control functions may be configured to be achieved by a program executed by the CPU 101 or other general-purpose CPUs. Alternatively, part of the above-described control functions may be configured to be achieved by dedicated hardware, such as another FPGA different from the control FPGA 110 and an application specific integrated circuit (ASIC).

The recording head 6 is driven by the recording head driver 104 that is controlled for operations by the CPU 101 and the control FPGA 110 and ejects ink onto the recording medium M on the platen 16 to form an image.

The encoder sensor 13 outputs an encoder value obtained through detection of a mark on the encoder sheet 14 to the control FPGA 110. This encoder value is transmitted from the control FPGA 110 to the CPU 101 and used, for example, for calculating the position and speed of the carriage 5. Using the position and the speed of the carriage 5 calculated from the encoder value, the CPU 101 generates and outputs a control command for controlling the main-scanning motor 8.

As described earlier, during the color adjustment the image forming apparatus 100, the colorimetric camera 20 captures images of both the colorimetric patterns formed on the recording medium M and the reference chart 40 and, on the basis of the RGB values of the colorimetric patterns and the RGB value of each of the reference patches of the reference chart 40 obtained from the captured images, calculates a colorimetric value of the colorimetric patterns (a color specification value in the standard color space, for example, an L*a*b* value in the L*a*b* color space). The colorimetric value of the colorimetric patterns calculated by the colorimetric camera 20 is transmitted to the CPU 101 via the control FPGA 110. For a specific method for calculating the colorimetric value of the colorimetric patterns, the method disclosed in, for example, Japanese Patent Application Laid-open No. 2013-051671 may be used.

The colorimetric camera 20 also has a function of inspecting contamination on the covering member 31 described earlier. As described earlier, the covering member 31 has the function of preventing, for example, the ink mist from entering the housing 23 and sticking to, for example, the two-dimensional image sensor 25, the illumination light sources 30, and the reference chart 40. As ink mist sticks to the covering member 31, however, contamination occurs on the covering member 31 over time. The covering member 31, when seriously contaminated, may impede the colorimetry for the colorimetric patterns.

The colorimetric camera 20 thus performs a process for inspecting contamination on the covering member 31 at predetermined timing, such as timing before the performance of the colorimetry for the colorimetric patterns or at regularly scheduled timing. If it is determined that the covering member 31 is contaminated, the colorimetric camera 20 transmits the inspection result to the CPU 101 via the control FPGA 110. On receipt from the colorimetric camera 20 of the inspection result that the covering member 31 is contaminated, the CPU 101 informs an operator that the contamination occurs on the covering member 31 of the colorimetric camera 20 through, for example, a display on an operating panel (not illustrated), thereby prompting the operator to clean or replace the covering member 31.

Configuration of Control Mechanism for Colorimetric Camera

Figure 6:
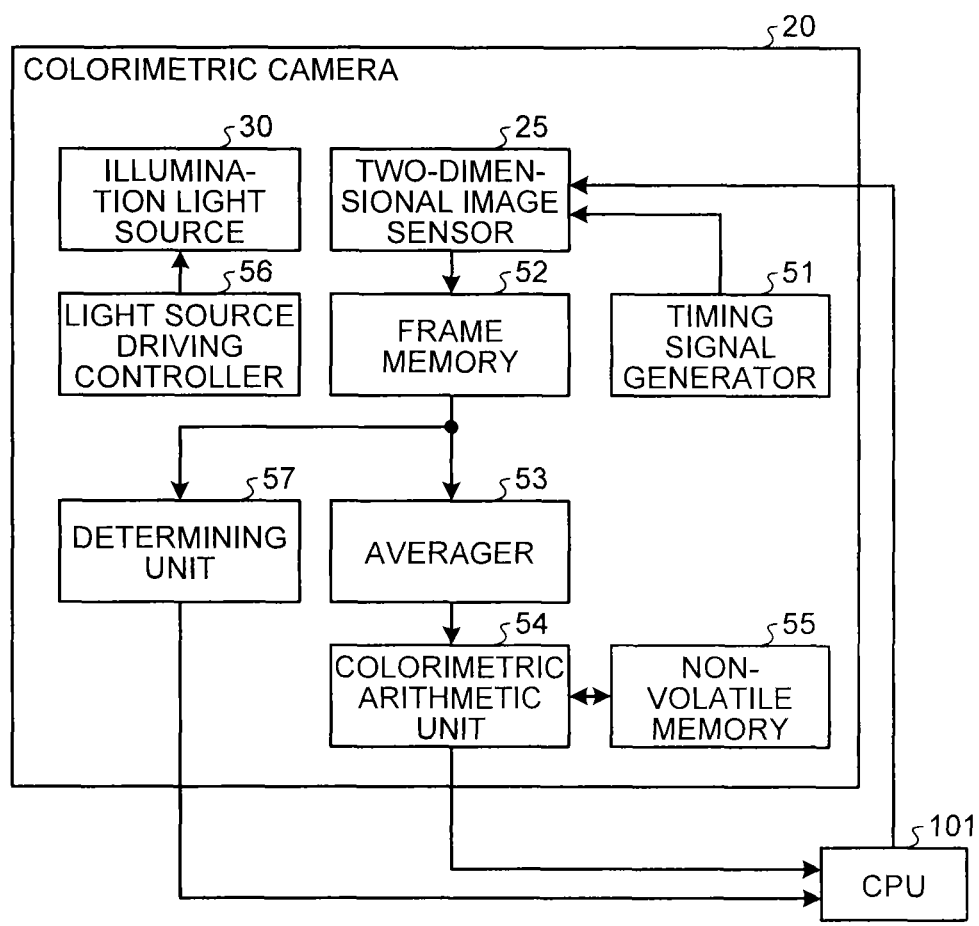
FIG. 6 is a block diagram illustrating an exemplary configuration of a control mechanism for the colorimetric camera.

The following describes in detail with reference to FIG. 6 a control mechanism for the colorimetric camera 20. FIG. 6 is a block diagram illustrating an exemplary configuration of the control mechanism for the colorimetric camera 20.

As illustrated in FIG. 6, the colorimetric camera 20 includes, in addition to the above-described two-dimensional image sensor 25 and the illumination light sources 30, a timing signal generator 51, a frame memory 52, an averager 53, a colorimetric arithmetic unit 51, a nonvolatile memory 55, a light source driving controller 56, and a determining unit 57.

The two-dimensional image sensor 25 converts light that is incident thereupon into a corresponding electric signal and outputs image data that represents an imaging area captured thereby. The two-dimensional image sensor 25 has built-in functions for performing AD conversion of converting an analog signal obtained through the photoelectric conversion to digital image data and performing various types of image processing for the image data, including shading correction, white balance correction, gamma correction, and image data format conversion and outputting the image data thereafter. Various operating conditions for the two-dimensional image sensor 25 are set in accordance with various types of setting signals from the CPU 101. The various types of image processing for the image data may be performed, in part or in whole, outside of the two-dimensional image sensor 25.

The timing signal generator 51 generates a timing signal that controls timing at which imaging by the two-dimensional image sensor 25 is to be started and supplies the two-dimensional image sensor 25 with the timing signal. In the present embodiment, the imaging by the two-dimensional image sensor 25 is performed not only for the performance of colorimetry for the colorimetric patterns, but also for the inspection of the covering member 31 for contamination. During the times of the performance of colorimetry for the colorimetric patterns and the inspection of the covering member 31 for contamination, the timing signal generator 51 generates the timing signal for controlling the timing to start the imaging by the two-dimensional image sensor 25 and supplies the two-dimensional image sensor 25 with the timing signal.

The frame memory 52 temporarily stores therein the image output from the two-dimensional image sensor 25.

When the colorimetry for the colorimetric patterns is performed, the averager 53 extracts, from the image that is output from the two-dimensional image sensor 25 and temporarily stored in the frame memory 52, a colorimetric target area set near the center of an area in which the colorimetric patterns are imaged and an area in which each of the reference patches on the reference chart 40 is imaged. The averager 53 averages image data of the extracted colorimetric target area and outputs the averaged value thus obtained as an RGB value of the colorimetric patterns to the colorimetric arithmetic unit 54. The averager 53 also averages image data of the area in which the reference patches are imaged and outputs the averaged value thus obtained as an RGB value of each reference patch to the colorimetric arithmetic unit 54.

Figure 7:
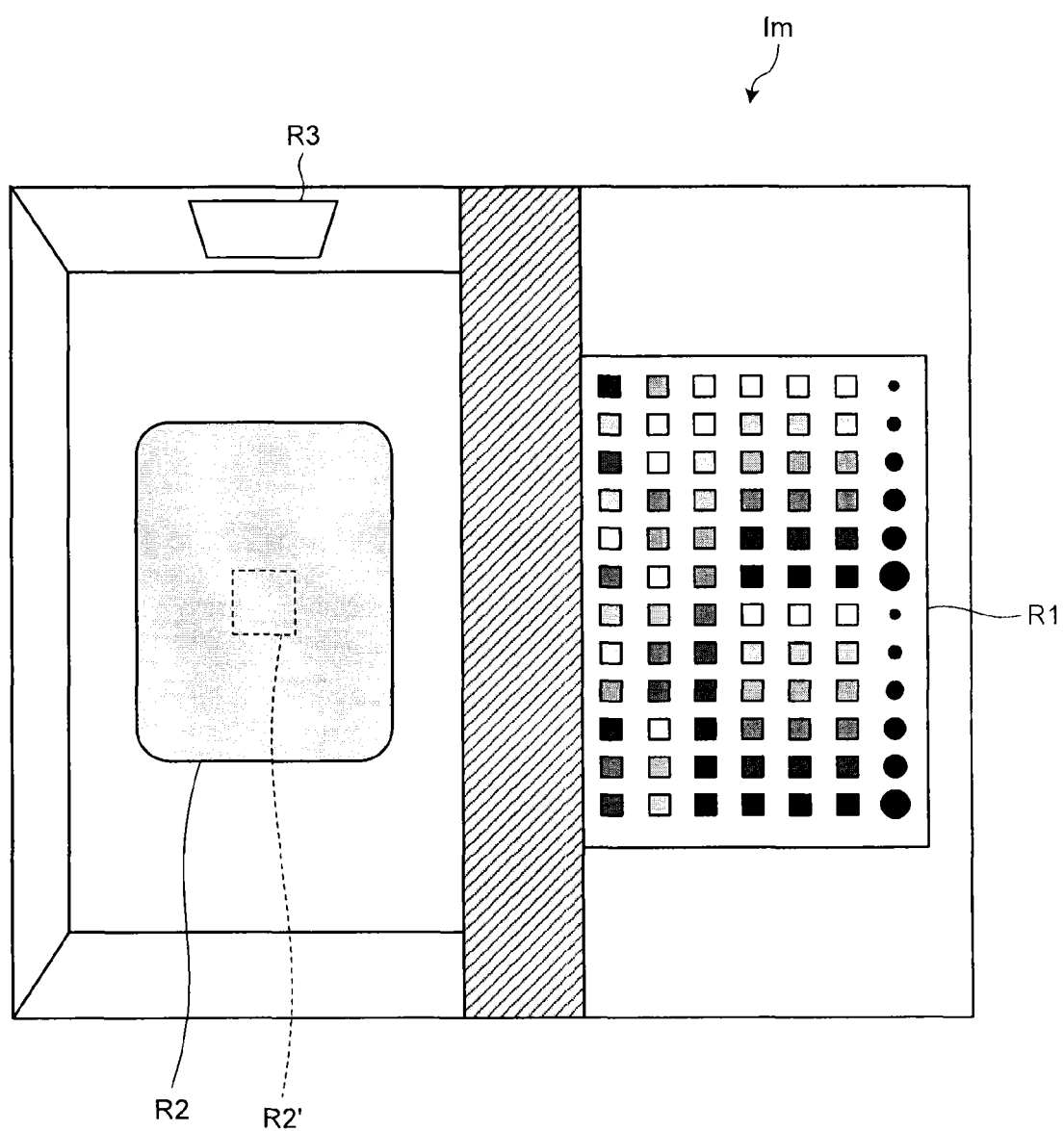
FIG. 7 is a diagram illustrating an exemplary image captured by a two-dimensional image sensor.

FIG. 7 is a diagram illustrating an exemplary image Im captured by the two-dimensional image sensor 25. As illustrated in FIG. 7, the image Im captured by the two-dimensional image sensor 25 includes a reference chart area R1, a pattern area R2, and a contamination inspection area R3. The reference chart area R1 represents the image of the reference chart 40. The pattern area R2 represents the image of the colorimetric patterns. The contamination inspection area R3 represents the image of the reference member 32. The pattern area R2 includes a colorimetric target area R2' set at a position near the center of the pattern area R2.

The averager 53 calculates the RGB value of the colorimetric patterns using the image data of the colorimetric target area R2' within the image Im as exemplified in FIG. 7. The averager 53 further calculates the RGB value of each reference patch using the image data of each reference patch in the reference chart area R1 within the image Im exemplified in FIG. 7.

Using the RGB value of the colorimetric patterns and the RGB value of each reference patch on the reference chart 40 obtained through the processing performed by the averager 53, the colorimetric arithmetic unit 54 calculates a colorimetric value of the colorimetric patterns. The colorimetric value of the colorimetric patterns calculated by the colorimetric arithmetic unit 54 is transmitted to the CPU 101 on the main control board 120. It is noted that the colorimetric arithmetic unit 54 can calculate the colorimetric value of the colorimetric patterns using, for example, the method disclosed in Japanese Patent Application Laid-open No. 2013-051671 and a detailed description of the processing performed by the calorimetric arithmetic unit 54 is herein omitted.

The nonvolatile memory 55 stores therein various types of data required by the colorimetric arithmetic unit 54 to calculate the colorimetric value of the colorimetric patterns.

The light source driving controller 56 generates a light source driving signal for driving the illumination light sources 30 and supplies the illumination light sources 30 with the light source driving signal. In the present embodiment, imaging by the two-dimensional image sensor 25 is performed not only for the colorimetry for the colorimetric patterns, but also for the inspection of contamination on the covering member 31. At each of these timings at which the two-dimensional image sensor 25 performs imaging, the light source driving controller 56 supplies the illumination light sources 30 with the light source driving signal to thereby turn on the illumination light sources 30.

The determining unit 57 determines, using the image data of the contamination inspection area R3 included in the image Im captured by the two-dimensional image sensor 25, whether the covering member 31 is contaminated. As described earlier, the contamination inspection area R3 represents an image of the reference member 32 captured by the two-dimensional image sensor 25, or more specifically, an imaged area (an inspection image) of the light (the inspection light) diffused and reflected on the surface of the reference member 32 that is incident upon the two-dimensional image sensor 25.

The light diffused and reflected on the surface of the reference member 32 (the inspection light) transmits the covering member 31 and is incident upon the two-dimensional image sensor 25. Thus, when the covering member 31 is contaminated with ink mist deposited thereon, the inspection light that is incident upon the two-dimensional image sensor 25 is affected by the ink mist affixed to the covering member 31. As a result, contamination on the covering member 31 can be determined on the basis of the image data of the contamination inspection area R3 that represents the image of the reference member 32. It is noted that the covering member 31 is determined to be contaminated as follows. Specifically, the covering member 31 is determined to be contaminated when it is so contaminated as to impede the colorimetry for the colorimetric patterns and is determined to be not contaminated when it is only slightly contaminated.

Figure 8:
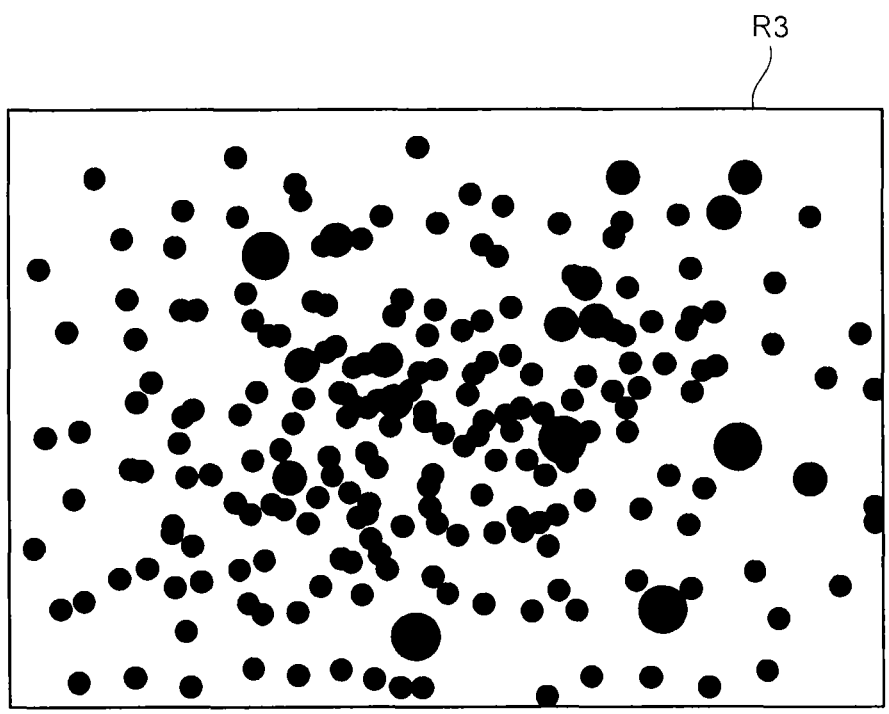
FIG. 8 is a diagram illustrating an exemplary image of a contamination inspection area.

FIG. 8 is a diagram illustrating an exemplary image of the contamination inspection area R3 when the covering member 31 is contaminated. When the covering member 31 is contaminated with a large amount of ink mist deposited thereto, a large number of dots with small luminances appear on the image of the contamination inspection area R3 as illustrated in FIG. 8. The greater the percentage occupied by the dots with small luminances within the image of the contamination inspection area R3, the more seriously the covering member 31 is contaminated. Thus, the covering member 31 can be determined to be contaminated by finding an area ratio of pixels having small pixel values (luminance values) within the image of the contamination inspection area R3 (the ratio of the pixels having small pixel values to the entire contamination inspection area R3) and by determining whether the area ratio is equal to or smaller than a predetermined threshold.

When inspecting the covering member 31 for contamination, the determining unit 57 extracts the image of the contamination inspection area R3 from the image Im that is output from the two-dimensional image sensor 25 and temporarily stored in the frame memory 52. The determining unit 57 finds, in the contamination inspection area R3, the area ratio of the pixels having the pixel values (luminance values) smaller than a reference value. If the area ratio thus obtained is equal to or greater than a first threshold, the determining unit 57 determines that the covering member 31 is contaminated. If the area ratio thus obtained is smaller than the first threshold, the covering member 31 is not contaminated. When the determining unit 57 determines that the covering member 31 is contaminated, the information is transmitted as an inspection result to the CPU 101 on the main control board 120.

Figure 9:
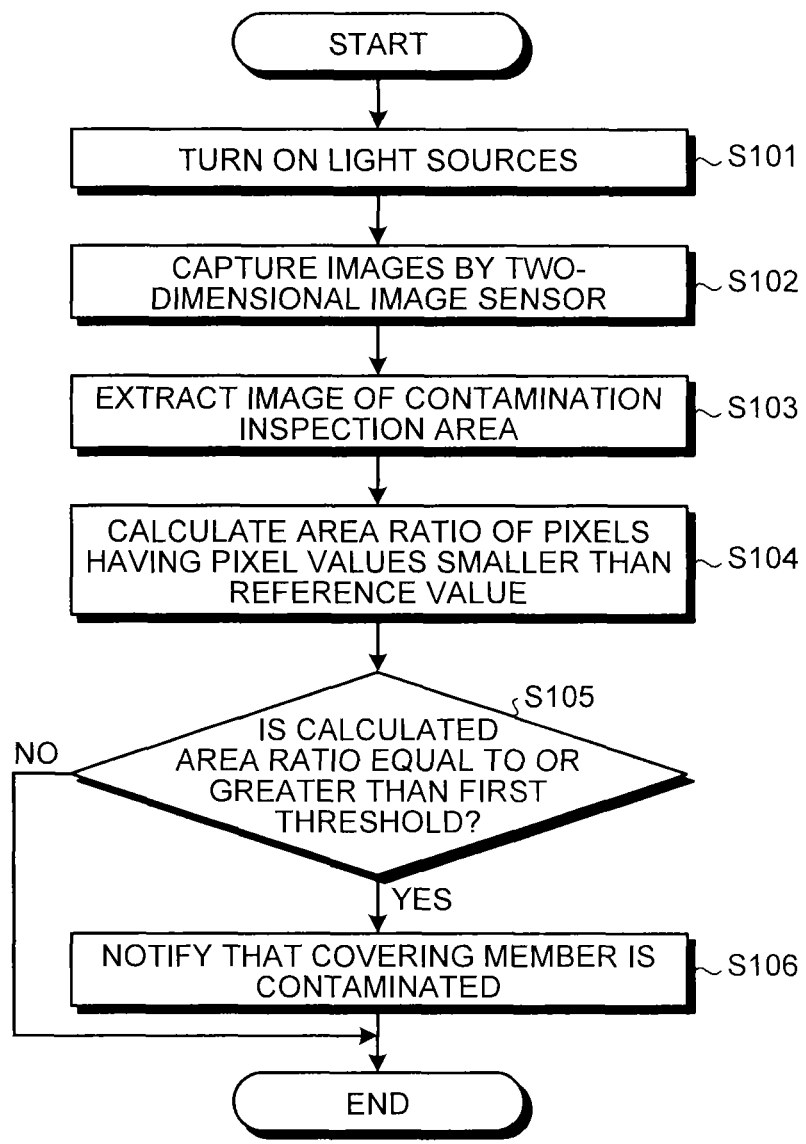
FIG. 9 is a flowchart illustrating an exemplary process for inspecting contamination on a covering member.

FIG. 9 is a flowchart illustrating an exemplary process for inspecting contamination on the covering member 31. The process illustrated by the flowchart of FIG. 9 is started at timing predetermined as inspection timing.

The light source driving controller 56 supplies the illumination light sources 30 with the light source driving signal to thereby turn on the illumination light sources 30 (Step S101).

The two-dimensional image sensor 25 captures images under the illumination provided by the illumination light sources 30 (Step S102). The images include the image of the contamination inspection area R3 (the inspection image) obtained when the two-dimensional image sensor 25 captures the image of the light (the inspection light) diffused and reflected on the surface of the reference member 32.

The determining unit 57 extracts the image of the contamination inspection area R3 from the images captured at Step S102 (Step S103).

The determining unit 57 analyzes the image of the contamination inspection area R3 extracted at Step S103 and calculates the area ratio of pixels having pixel values smaller than the reference value within the image of the contamination inspection area R3 (the ratio of the pixels having the pixel values smaller than the reference value to the entire contamination inspection area R3) (Step S104).

The determining unit 57 then determines whether or not the area ratio calculated at Step S104 is equal to or greater than the first threshold (Step S105). If it is determined that the area ratio calculated at Step S104 is equal to or greater than the first threshold (Yes at Step S105), the determining unit 57 transmits an inspection result that indicates that the covering member 31 is contaminated to the CPU 101. As a result, the operator is notified that the covering member 31 of the colorimetric camera 20 is contaminated through, for example, a display on the operating panel not illustrated, as controlled by the CPU 101 (Step S106). If it is determined that the area ratio calculated at Step S104 is smaller than the first threshold (No at Step S105), the determining unit 57 terminates the process without notifying the operator.

It has been described above that the dots with small luminances appear on the image of the contamination inspection area R3 when the covering member 31 is contaminated. It should, however, be noted that, depending on positional relations of the covering member 31 and the reference member 32 relative to the two-dimensional image sensor 25, the contamination on the covering member 31 may appear as reduced luminances over a wide area in the image of the contamination inspection area R3, not as the dots with small luminances in the image of the contamination inspection area R3.

Figure 10:
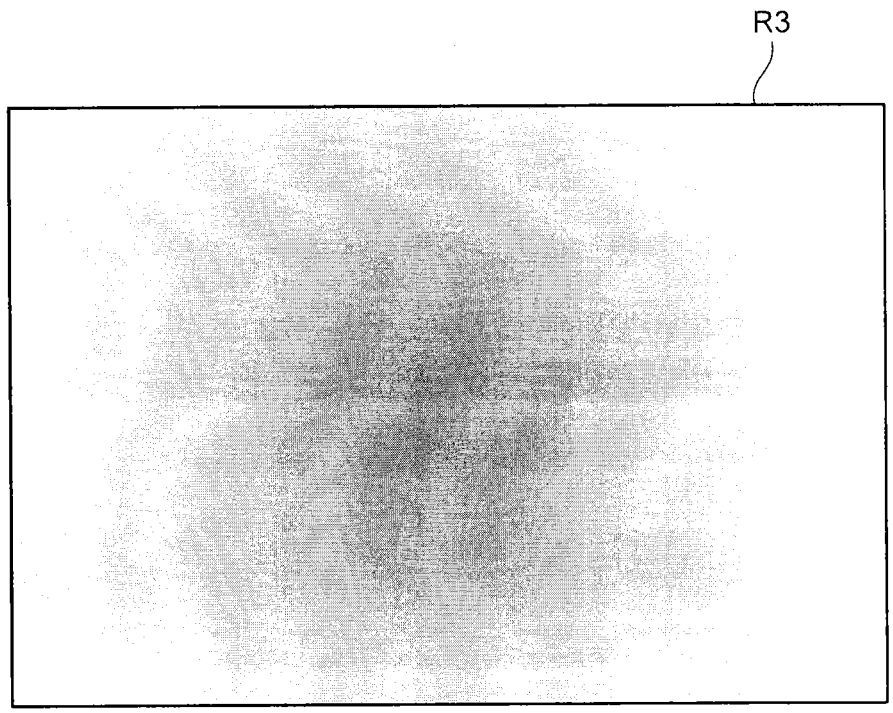
FIG. 10 is a diagram illustrating another exemplary image of a contamination inspection area.

FIG. 10 is a diagram illustrating another exemplary image of the contamination inspection area R3 when the covering member 31 is contaminated. In the example illustrated in FIG. 10, the contamination on the covering member 31 appears as reduced luminances over a wide area in the image of the contamination inspection area R3. Thus, the determining unit 57 may be configured, instead of or in addition to the above-described determining method, so as to find an average luminance in the contamination inspection area R3 to thereby determine whether or not the covering member 31 is contaminated according to whether or not the average luminance is equal to or smaller than a predetermined threshold (a second threshold).

Figure 11:
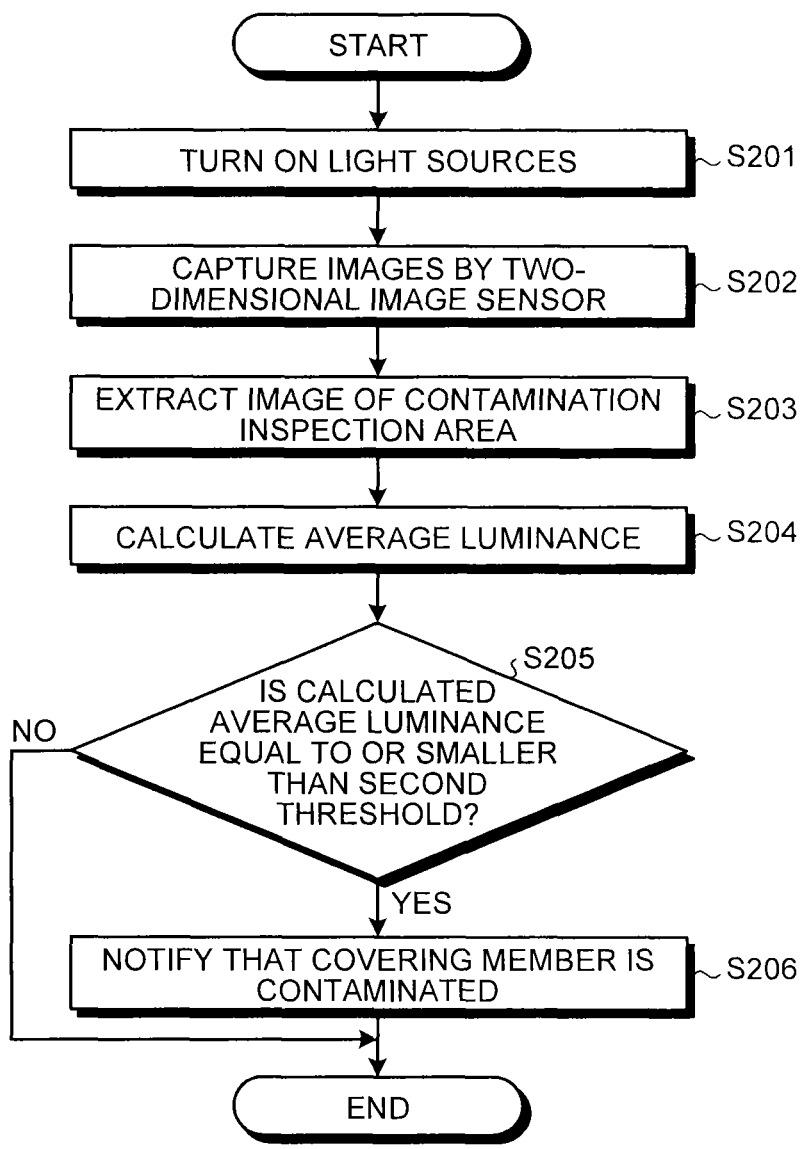
FIG. 11 is a flowchart illustrating another exemplary process for inspecting contamination on the covering member.

FIG. 11 is a flowchart illustrating another exemplary process for inspecting contamination on the covering member 31. The process illustrated by the flowchart of FIG. 11 is started at timing predetermined as inspection timing.

The light source driving controller 56 supplies the illumination light sources 30 with the light source driving signal to thereby turn on the illumination light sources 30 (Step S201).

The two-dimensional image sensor 25 captures images under the illumination provided by the illumination light sources 30 (Step S202). The images include the image of the contamination inspection area R3 (the inspection image) obtained when the two-dimensional image sensor 25 captures the image of the light (the inspection light) diffused and reflected on the surface of the reference member 32.

The determining unit 57 extracts the image of the contamination inspection area R3 from the images captured at Step S202 (Step S203). The determining unit 57 then calculates the average luminance of the image of the contamination inspection area R3 extracted at Step S203 (Step S204).

The determining unit 57 determines whether or not the average luminance calculated at Step S204 is equal to or smaller than the second threshold (Step S205). If it is determined that the average luminance calculated at Step S204 is equal to or smaller than the second threshold (Yes at Step S205), the determining unit 57 transmits an inspection result that indicates that the covering member 31 is contaminated to the CPU 101. As a result, the operator is notified that the covering member 31 of the colorimetric camera 20 is contaminated through, for example, the display on the operating panel (not illustrated), as controlled by the CPU 101 (Step S206). If it is determined that the average luminance calculated at Step S204 exceeds the second threshold (No at Step S205), the determining unit 57 terminates the process without notifying the operator.

The control functions of the different elements that constitute the image forming apparatus 100 or the colorimetric camera 20 according to the present embodiment described above can be achieved using hardware, software, or both combined. When the control functions of the different elements that constitute the image forming apparatus 100 or the colorimetric camera 20 according to the present embodiment are to be achieved using software, a processor of the image forming apparatus 100 or the colorimetric camera 20 executes a program that describes a processing sequence. The program executed by the processor is provided by, for example, being incorporated in an internal ROM or the like of the image forming apparatus 100 or the colorimetric camera 20. Alternatively, the program executed by the processor is recorded and provided in a computer-readable recording medium such as a CD-ROM, flexible disk, a CD-R, and a DVD, as a file having an installable or executable format.

The program executed by the processor may even be stored in a computer connected to a network such as the Internet and provided by being downloaded via the network. Still alternatively, the program executed by the processor may be provided or distributed via a network such as the Internet.

Advantageous Effects of Embodiment

As described in detail above with reference to the specific examples, the colorimetric camera 20 in the present embodiment (an example of an imaging device) includes the reference member 32 (an example of a contamination inspection member) that is disposed between the opening 24 in the housing 23 and the covering member 31 and that causes the inspection light for inspecting contamination on the covering member 31 to be incident upon the two-dimensional image sensor 25 via the covering member 31. The colorimetric camera 20 can thus appropriately determine whether or not the covering member 31 is contaminated on the basis of the image (the image of the contamination inspection area R3) obtained by the two-dimensional image sensor 25 when it captures the image of the inspection light (the light diffused and reflected on the surface of the reference member 32), so that the covering member 31 can be conveniently inspected for contamination.

Specifically, the known method disclosed in Japanese Patent Application Laid-open No. 2013-207595 requires that two images with different distances between the recording medium and the housing be captured and analyzed in order to inspect the optical member for contamination. This approach is taken to determine whether a low luminance portion that appears on the image is attributable to contamination on the optical member or on the recording medium. In contrast, the colorimetric camera 20 in the present embodiment is configured such that the inspection light from the reference member 32 disposed between the opening 24 in the housing 23 and the covering member 31 is caused to be incident upon the two-dimensional image sensor 25 via the covering member 31. As a result, when the covering member 31 is contaminated, the reference member 32 is similarly contaminated, so that the need is eliminated to determine the cause of the low luminance portion that appears on the image. Thus, the contamination on the covering member 31 can be appropriately determined by the convenient method of, for example, comparing the area ratio of pixels having small luminances within the image of the contamination inspection area R3 or the average luminance with a predetermined threshold using a single image obtained through a single imaging operation. The contamination on the covering member 31 can thus be conveniently inspected. It is noted that the ink mist that enters the housing 23 through the opening 24 in the housing 23 sticks to the covering member 31 by Coulomb's force. As a result, when the ink mist sticks to the covering member 31, it similarly sticks to the reference member 32 disposed between the opening 24 and the covering member 31.

In the colorimetric camera 20 according to the present embodiment, the reference member 32 may be disposed at a position outside the optical path of the light that is reflected off the colorimetric patterns and is incident upon the two-dimensional image sensor 25 through the opening 24, for example, on the inner wall portion of the housing 23 between the opening 24 and the covering member 31. This arrangement can effectively prevent inconvenience of fluctuating RGB values of the colorimetric patterns as affected by the diffused and reflected light at the reference member 32 during the performance of colorimetry for the colorimetric patterns.

The image forming apparatus 100 in the present embodiment includes the colorimetric camera 20 that has the function of inspecting the covering member 31 for contamination as described above. The image forming apparatus 100 can thus perform color adjustments in accordance with the colorimetric values of the calorimetric patterns calculated highly accurately by the colorimetric camera 20, thereby outputting an image with high reproducibility.

First Modification

The embodiment described above includes, as an exemplary contamination inspection member that causes the inspection light to be incident upon the two-dimensional image sensor 25 via the covering member 31, the reference member 32 that diffuses and reflects light from the illumination light sources 30 and causes the resultant light to be incident upon the two-dimensional image sensor 25 as the inspection light. The contamination inspection member is, however, required only to be configured so as to cause the inspection light to be incident upon the two-dimensional image sensor 25 via the covering member 31. Thus, another possible candidate for the contamination inspection member may, for example, be an inspection light source that irradiates the covering member 31 with light and causes light transmitting the covering member 31 to be incident upon the two-dimensional image sensor 25 as the inspection light.

Figure 12:
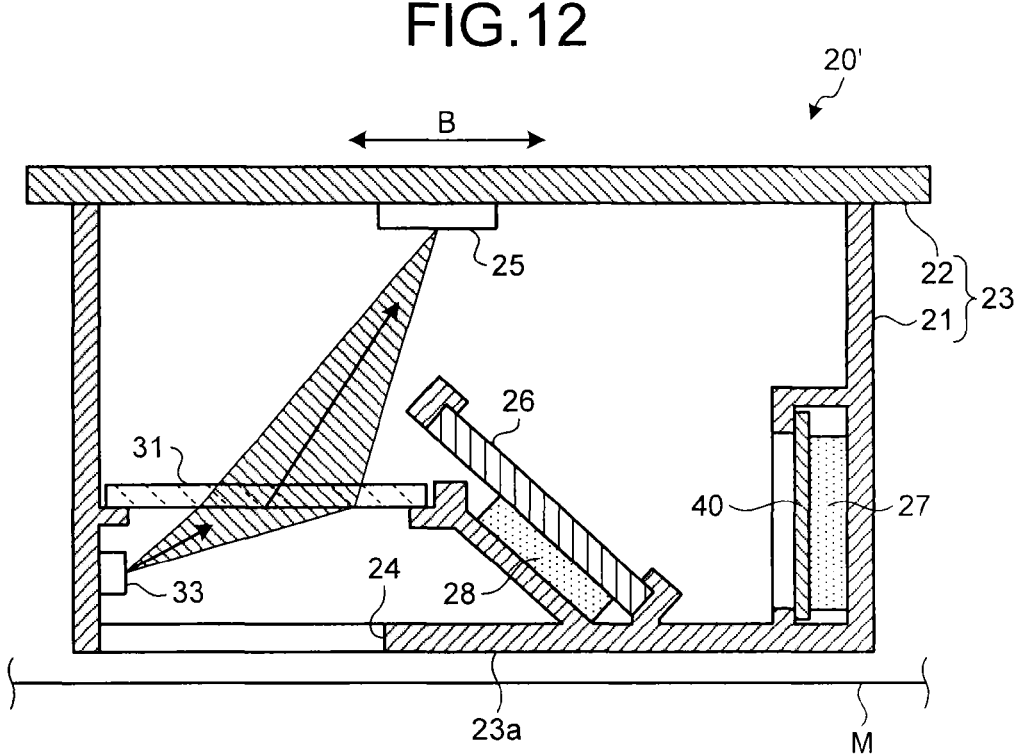
FIG. 12 is a longitudinal sectional view illustrating a colorimetric camera according to a first modification.

FIG. 12 is a longitudinal sectional view illustrating a colorimetric camera 20' according to a first modification. As illustrated in FIG. 12, the colorimetric camera 20' includes an inspection light source 33 instead of the reference member 32 included in the colorimetric camera 20 according to the embodiment described earlier. The colorimetric camera 20' in the first modification is otherwise similarly configured as in the above-described colorimetric camera 20 according to the embodiment.

The inspection light source 33 emits light with a light source driving signal supplied from the above-mentioned light source driving controller 56 to thereby irradiate the covering member 31 with light. Light that has transmitted the inspection light source 33 (diffused light) is caused, as the inspection light, to be incident upon the two-dimensional image sensor 25.

The determining unit 57 of the colorimetric camera 20' can determine whether or not the covering member 31 is contaminated using a method identical to the above-described method on the basis of the inspection image (the image of the contamination inspection area R3) obtained by the two-dimensional image sensor 25 when it captures the image of the inspection light. In the first modification, however, the contamination inspection area R3 represents an area of the image of the covering member 31 irradiated with light from the inspection light source 33.

Preferably, the inspection light source 33 is configured to include an intensity controller that changes the intensity of the light illuminating the covering member 31. This configuration allows images to be captured a plurality of times, each image capturing being performed with unique intensity of light with which the inspection light source 33 irradiates the covering member 31 (specifically, the intensity of the inspection light). The images thus obtained enable inspection of the contamination on the covering member 31 even more accurately.

Figure 13:
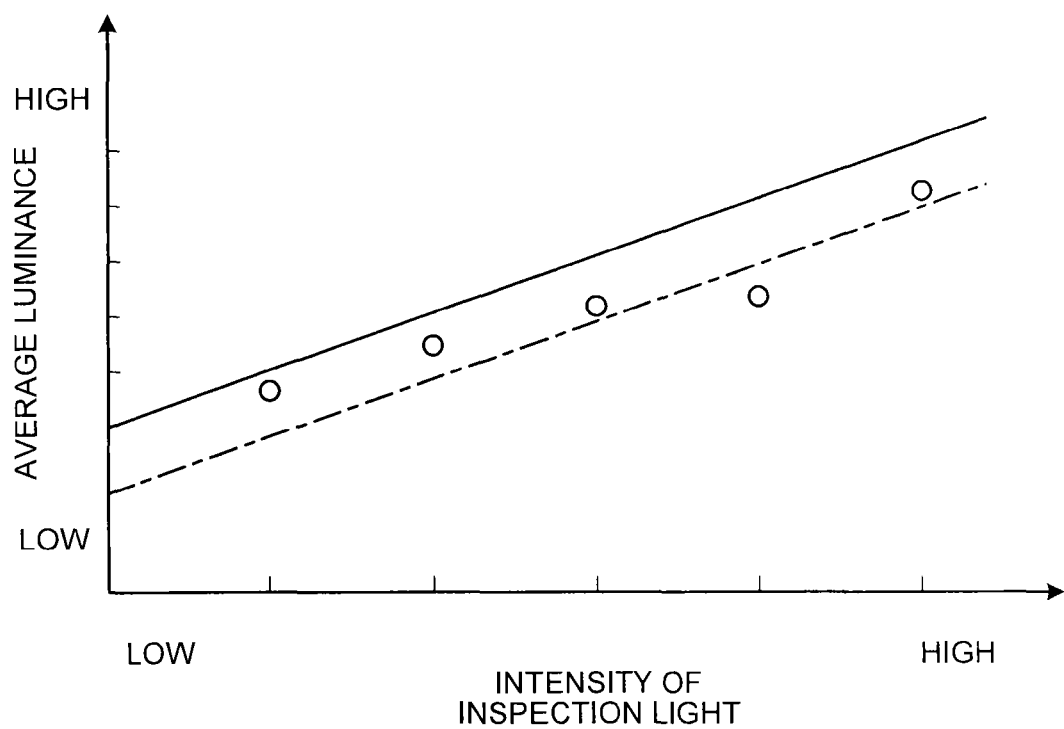
FIG. 13 is a graph illustrating a process for determining contamination while changing the intensity of inspection light.

FIG. 13 is a graph illustrating a process for determining the contamination while changing the intensity of the inspection light. FIG. 13 illustrates an example in which the average luminance of the contamination inspection area R3 is compared with the second threshold to thereby determine whether the covering member 31 is contaminated. To determine whether or not the covering member 31 is contaminated by changing the intensity of the inspection light, a relation between the intensity of the inspection light and the average luminance of the contamination inspection area R3 is found in advance under a condition in which the covering member 31 is not contaminated. When the covering member 31 is not contaminated, the average luminance of the contamination inspection area R3 increases at greater intensity levels of the inspection light (the solid line in FIG. 13). Thus, the second threshold is established according to the intensity of the inspection light (the dash-single-dot line in FIG. 13). During the inspection of the covering member 31 for contamination, image capturing is performed a plurality of times with different intensity levels of the inspection light and the average luminance of the contamination inspection area R3 included in each image is compared with the second threshold varying according to the intensity of the inspection light. If any one of the average luminances is equal to or smaller than the second threshold, the covering member 31 is determined to be contaminated.

In the first modification, the covering member 31 is inspected for contamination using the images obtained through the image capturing performed a plurality of times while changing the intensity levels of the inspection light as described above. This approach enables detection of contamination that does not appear as a reduced luminance of the image depending on the intensity of the inspection light, so that the contamination on the covering member 31 can be inspected more accurately. In the first modification, the covering member 31 is inspected for contamination using a plurality of images; however, the first modification eliminates the need for changing the position of the housing 23, unlike the known method disclosed in Japanese Patent Application Laid-open No. 2013-207595. Furthermore, the contamination on the covering member 31 can be appropriately determined through a convenient method by which the average luminance (or the area ratio of the low luminance portion) of the contamination inspection area R3 is compared with the threshold, so that the contamination on the covering member 31 can be conveniently inspected.

As described above, in the first modification, the contamination inspection area R3 represents the area of the image of the covering member 31 irradiated with the light from the inspection light source 33. It should therefore be noted that the contamination inspection area R3 also includes an image area of a subject outside the housing 23 captured through the opening 24 (the image area that represents the pattern area R2 illustrated in FIG. 7 during the colorimetry for the colorimetric patterns). As a result, if the subject (for example, the recording medium M) disposed as a background outside the housing 23 is contaminated during the inspection of the covering member 31 for contamination, the contamination on the subject as the background may affect the inspection to cause a false determination of a contaminated covering member 31 when the covering member 31 is not contaminated.

Thus, in the first modification that includes the inspection light source 33 as the contamination inspection member, preferably, the inspection light source 33 irradiates the covering member 31 with light to thereby cause the inspection light to be incident upon the two-dimensional image sensor 25 for the performance of the contamination inspection for the covering member 31 while the two-dimensional image sensor 25 is moving relative to the subject, specifically, while the colorimetric camera 20' is moving in the main-scanning direction as the carriage 5 moves or while the recording medium M as the subject is being conveyed. By performing the inspection while the two-dimensional image sensor 25 is moving relative to the subject as described above, effects from the contamination on the subject can be smoothed within the contamination inspection area R3 extracted from the image captured by the two-dimensional image sensor 25. Thus, when the determining unit 57 determines whether or not the covering member 31 is contaminated on the basis of a comparison made of the area ratio of pixels having pixel values (luminance values) equal to or smaller than the reference value in the contamination inspection area R3 against the first threshold, the effects from the contaminated subject can be reduced to thus enable an appropriate inspection of the contamination on the covering member 31.

The image forming apparatus 100 in the present embodiment performs, during an initial operation before the image formation on the recording medium M, what is called a paper width detecting process in which the image forming apparatus 100 moves the carriage 5 to thereby cause the colorimetric camera 20 (colorimetric camera 20') to capture an image with the recording medium M placed on the platen 16. The image forming apparatus 100 thereby determines positions of both ends in the width direction of the recording medium M and detects the width of the recording medium M on the basis of the captured image output from the two-dimensional image sensor 25. Thus, an arrangement that causes the covering member 31 to be irradiated with the light from the inspection light source 33 to thereby perform the inspection of the covering member 31 for contamination while this paper width detecting process is in progress eliminates the need for moving the colorimetric camera 20 or the recording medium M in order to perform the inspection of the covering member 31 for contamination. This arrangement thus can effectively prevent reduction in productivity as a result of the performance of the inspection of the covering member 31 for contamination.

Additionally, the image forming apparatus 100 in the present embodiment performs, during the initial operation before the image formation on the recording medium M, what is called a skew correcting process in which the image forming apparatus 100 reciprocates the recording medium M placed on the platen 16 in the sub-scanning direction to thereby correct any skew in the recording medium M. Thus, an arrangement that causes the covering member 31 to be irradiated with the light from the inspection light source 33 to thereby perform the inspection of the covering member 31 for contamination while this skew correcting process is in progress eliminates the need for moving the calorimetric camera 20' or the recording medium M in order to perform the inspection of the covering member 31 for contamination. This arrangement thus can effectively prevent reduction in productivity as a result of the performance of the inspection of the covering member 31 for contamination.

Second Modification

Figure 14A:
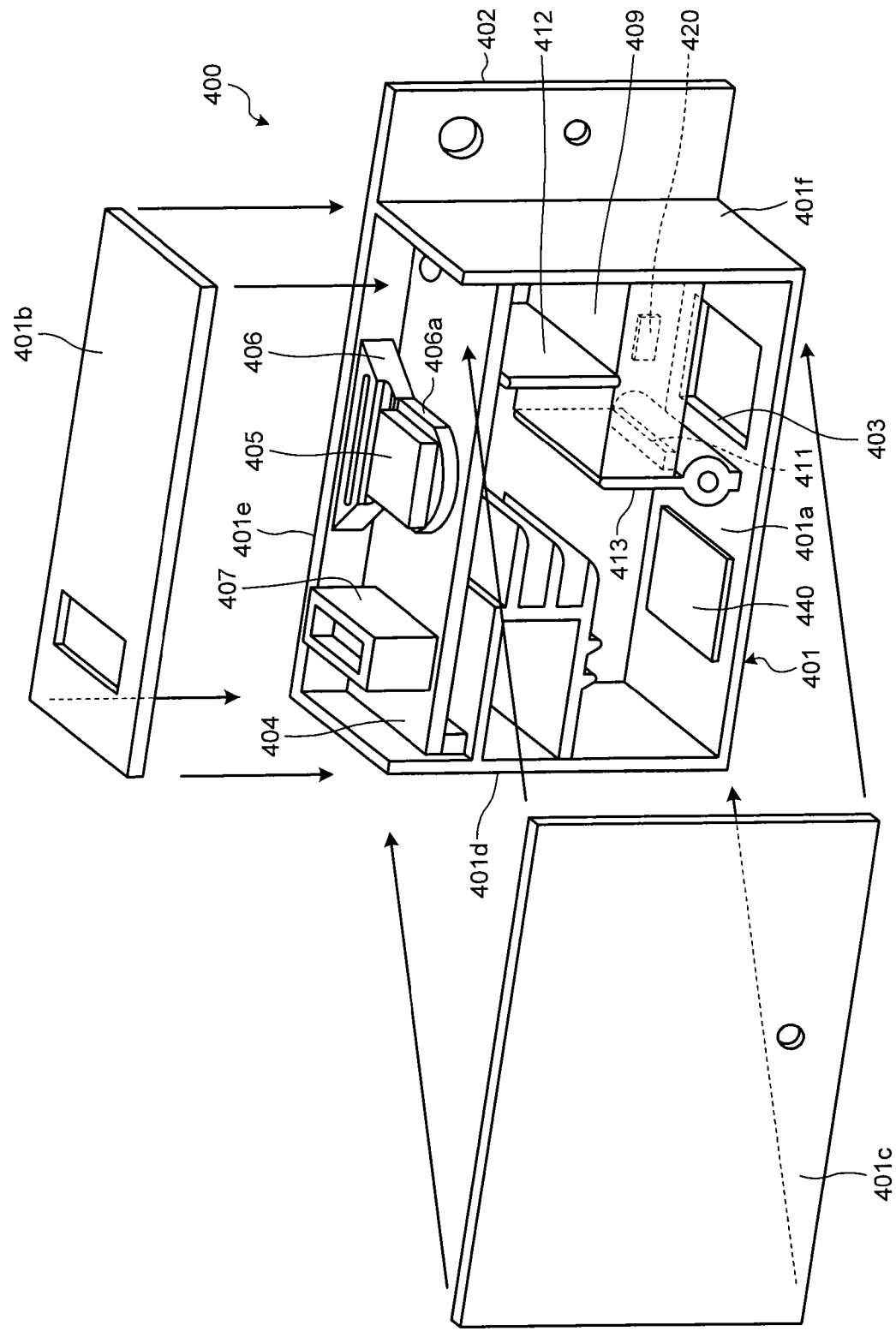
FIG. 14A is an exploded perspective view illustrating a colorimetric camera according to a second modification.
Figure 14B:
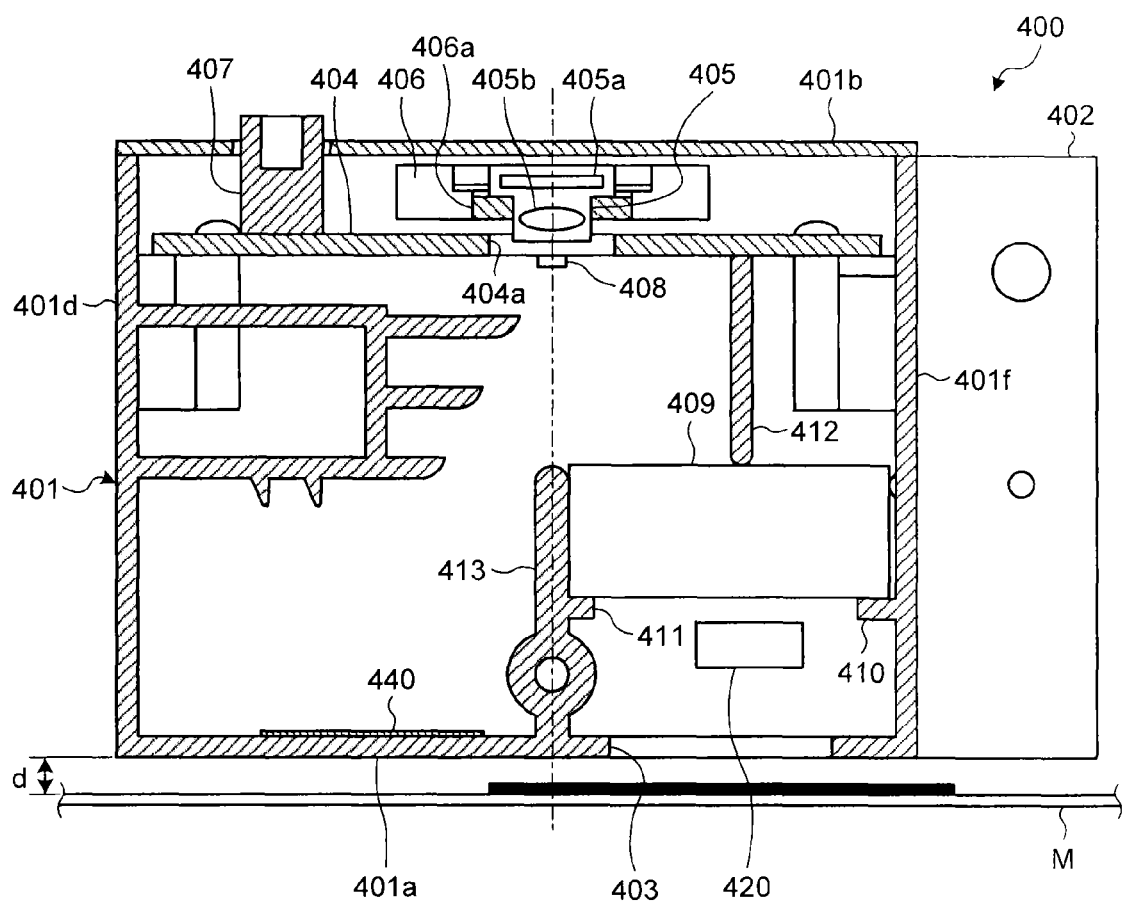
FIG. 14B is a longitudinal sectional view illustrating the colorimetric camera according to the second modification.

The above-described embodiment is an exemplary application of the present invention to the colorimetric camera 20 configured as illustrated in FIGS. 3A and 3B. The present invention is nonetheless effectively applicable to a colorimetric camera 400 configured, for example, as illustrated in FIGS. 14A and 14B. FIG. 14A is an exploded perspective view illustrating the colorimetric camera 400. FIG. 14B is a longitudinal sectional view illustrating the colorimetric camera 400. The colorimetric camera 400 is functionally identical to the colorimetric camera 20 described above. The colorimetric camera 400, however, has mechanical arrangements different from those of the colorimetric camera 20 described above. The following describes the mechanical arrangements of the colorimetric camera 400.

As illustrated in FIGS. 14A and 14B, the colorimetric camera 400 includes a housing 401 with which a mounting tab 402 is integrated. The housing 401 includes, for example, a bottom plate 401a, a top plate 401b, and side walls 401c, 401d, 401e, and 401f. The bottom plate 401a and the top plate 401b are opposed to each other with a predetermined distance therebetween. The side walls 401c, 401d, 401e, and 401f connect the bottom plate 401a to the top plate 401b. The bottom plate 401a and the side walls 401d, 401e, and 401f of the housing 401 are formed integrally with the mounting tab 402 by, for example, molding. The top plate 401b and the side wall 401c are removably attached to the bottom plate 401a and the side walls 401d, 401e, and 401f. FIG. 14A illustrates a condition in which the top plate 401b and the side wall 401c are detached.

The colorimetric camera 400 is mounted on the carriage 5 as follows, for example. Specifically, the colorimetric camera 400 is fastened to a side surface of the carriage 5 using a fastening member, such as a screw, with the side wall 401e and the mounting tab 402 of the housing 401 pressed against the side surface of the carriage 5. The foregoing procedure results in the colorimetric camera 400 being mounted on the carriage 5 such that, as illustrated in FIG. 14B, the bottom plate 401a of the housing 401 faces the recording medium M on the platen 16 with a predetermined distance d therebetween in a condition in which the bottom plate 401a extends substantially in parallel with the recording medium M.

The bottom plate 401a of the housing 401 facing the recording medium M on the platen 16 has an opening 403 (that corresponds to the opening 24 of the colorimetric camera 20 described earlier) that allows the image of the colorimetric patterns recorded on the recording medium M to be captured from the inside of the housing 401. In addition, a reference chart 440 (that corresponds to the reference chart 40 of the colorimetric camera 20 described earlier) is disposed on the inner surface side of the bottom plate 401a of the housing 401 so as to be adjacent to the opening 403 across a supporting member 413.

A circuit board 404 is disposed on the side of the top plate 401b inside the housing 401. A sensor unit 405 (that corresponds to the two-dimensional image sensor 25 of the colorimetric camera 20 described earlier) that captures an image is disposed between the top plate 401b of the housing 401 and the circuit board 404. As illustrated in FIG. 14B, the sensor unit 405 includes an image sensor 405a and an imaging forming lens 405b. Specifically, the image sensor 405a is, for example, a CCD sensor or a CMOS sensor. The imaging forming lens 405b forms an optical image of an imaging range of the sensor unit 405 on a light-receiving surface of the image sensor 405a.

The sensor unit 405 is held by, for example, a sensor holder 406 that is integrally formed with the side wall 401e of the housing 401. The sensor holder 406 has a ring portion 406a at a position opposed to a through hole 404a formed in the circuit board 404. The ring portion 406a has a through hole having a shape that follows an outline of a protruded portion of the sensor unit 405 on the side of the imaging forming lens 405b. The sensor unit 405 is held by the sensor holder 406 such that the imaging forming lens 405b faces the bottom plate 401a of the housing 401 through the through hole 404a in the circuit board 404 when the protruded portion of the sensor unit 405 on the side of the imaging forming lens 405b is passed through the ring portion 406a of the sensor holder 406.

At this time, the sensor unit 405 is held in position by the sensor holder 406 such that an optical axis indicated by the dash-single-dot line in FIG. 14B extends substantially perpendicularly to the bottom plate 401a of the housing 401 and the opening 403 and the reference chart 440 are encompassed in the imaging range. This condition allows the sensor unit 405 to capture an image of the subject outside the housing 401 through the opening 403 using one part of the imaging area and to capture an image of the reference chart 440 using another part of the imaging area.

The sensor unit 405 is electrically connected to the circuit board 404 on which various types of electronic components are mounted via, for example, a flexible cable. Additionally, the circuit board 404 has an external connector 407 to which a connecting cable for connecting the colorimetric camera 400 to the main control board 120 (see FIG. 5) of the image forming apparatus 100 is connected.

An illumination light source 408 (that corresponds to the illumination light sources 30 of the calorimetric camera 20 described earlier) that illuminates at least the imaging range of the sensor unit 405 is disposed inside the housing 401.

Additionally, an optical path length changing member 409 is disposed inside the housing 401 in an optical path midway between the sensor unit 405 and the subject outside the housing 401 imaged by the sensor unit 405 through the opening 403. The optical path length changing member 409 assumes an optical element having a refractive index of n to offer a sufficient transmissivity to light (illumination light) from the illumination light source 408. The optical path length changing member 409 functions to bring an image forming surface of the optical image of the subject outside the housing 401 close to an image forming surface of the optical image of the reference chart 440 inside the housing 401. Specifically, the colorimetric camera 400 in the second modification includes the optical path length changing member 409 disposed in the optical path midway between the sensor unit 405 and the subject outside the housing 401 to thereby change the optical length, thereby focusing both the image forming surface of the optical image of the subject outside the housing 401 and the image forming surface of the optical image of the reference chart 440 inside the housing 401 on the light-receiving surface of the image sensor 405a of the sensor unit 405. The foregoing arrangement enables the sensor unit 405 to capture focused images of both the subject outside the housing 401 and the reference chart 440 inside the housing 401.

Reference is made to FIGS. 14A and 14B. The optical path length changing member 409 has a surface on the side of the bottom plate 401a supported on both ends by a pair of ribs 410 and 411. Additionally, a holding member 412 is disposed between a surface of the optical path length changing member 409 on the side adjacent the top plate 401b and the circuit board 404. The pair of ribs 410 and 411 and the holding member 412 together keep the optical path length changing member 409 stationary inside the housing 401. The optical path length changing member 409 is disposed so as to close the opening 403 in the bottom plate 401a of the housing 401. This disposition of the optical path length changing member 409 results in the optical path length changing member 409 having a further function (that corresponds to the function of the covering member 31 of the colorimetric camera 20 described earlier) of preventing impurities including ink mist and dust and dirt that enter the housing 401 through the opening 403 from the outside of the housing 401 from sticking to, for example, the sensor unit 405, the illumination light source 408, and the reference chart 440.

In the colorimetric camera 400 of the second modification, the optical path length changing member 409 is the optical member subject to the contamination inspection. Specifically, in the colorimetric camera 400 of the second modification, the above-described determining unit 57 (see FIG. 6) determines whether or not the optical path length changing member 409 is contaminated on the basis of the image captured by the sensor unit 405 of inspection light that transmits the optical path length changing member 409.

The colorimetric camera 400 of the second modification includes a reference member 420 as an exemplary contamination inspection member that causes the inspection light for inspecting the optical path length changing member 409 for contamination to be incident upon the sensor unit 405 (the image sensor 405a of the sensor unit 405) via the optical path length changing member 409. The reference member 420 is disposed between the opening 403 in the housing 401 and the optical path length changing member 409. As with the reference member 32 of the colorimetric camera 20 described earlier, for example, the reference member 420 is formed into a thin plate having an even white surface and serves as a reflecting member, diffusing and reflecting light from the illumination light source 408 on its white surface and causing the resultant light to be incident upon the sensor unit 405 as the inspection light. Again as with the reference member 32 of the colorimetric camera 20 described earlier, the reference member 420 may have any color other than white when the color is identifiable from the ink mist sticking to the optical path length changing member 409.

The reference member 420 is preferably disposed at a position outside the optical path of the light that is reflected off the colorimetric patterns and that is incident upon the sensor unit 405 via the opening 403 when the sensor unit 405 captures an image of the colorimetric patterns illuminated by the illumination light source 408. For example, as illustrated in FIGS. 14A and 14B, the reference member 420 is bonded to an inner surface of the side wall 401*e* between the opening 403 and the optical path length changing member 409, having a surface opposite to the white surface as a bonding surface. This arrangement can effectively prevent inconvenience of fluctuating RGB values of the colorimetric patterns as affected by the diffused and reflected light at the reference member 420 during the performance of colorimetry for the colorimetric patterns. It is noted that the reference member 420 is required only to be disposed at a position outside the optical path of the light that is reflected off the colorimetric patterns and is incident upon the sensor unit 405 and the reference member 420 does not necessarily have to be bonded to the inner surface of the side wall 401*e*.

It is noted that, as with the colorimetric camera 20' described as the first modification, the colorimetric camera 400 in the second modification may be configured to use as the contamination inspection member, instead of the reference member 420, an inspection light source that irradiates the optical path length changing member 409 with light and causes light transmitting the optical path length changing member 409 to be incident upon the sensor unit 405 as the inspection light.

Third Modification

In the embodiment and the first and second modifications described above, the colorimetric camera 20 (or the colorimetric camera 400) has the function (of the determining unit 57) of determining whether or not the covering member 31 (or the optical path length changing member 409) is contaminated on the basis of the inspection image obtained through the imaging of the inspection light by the two-dimensional image sensor 25 (or the sensor unit 405). A configuration may nonetheless be implemented to cause the foregoing determination to be made outside of the colorimetric camera 20 (or the calorimetric camera 400). For example, the CPU 101 or the control FPGA 110 mounted on the main control board 120 of the image forming apparatus 100 may be configured to perform the function of the determining unit 57. In this case, the colorimetric camera 20 (or the colorimetric camera 400) transmits the inspection image captured by the two-dimensional image sensor 25 (or the sensor unit 405) to the CPU 101 or the control FPGA 110 and the CPU 101 or the control FPGA 110 determines whether or not the covering member 31 included in the colorimetric camera 20 (or the optical path length changing member 409 included in the colorimetric camera 400) is contaminated using the inspection image transmitted from the colorimetric camera 20 (or the colorimetric camera 400).

Fourth Modification

Another configuration may be implemented to cause an external device connected to the image forming apparatus 100 to perform the function (of the determining unit 57) of determining whether or not the covering member 31 (or the optical path length changing member 409) is contaminated on the basis of the inspection image obtained through the imaging of the inspection light by the two-dimensional image sensor 25 (or the sensor unit 405).

Figure 15:
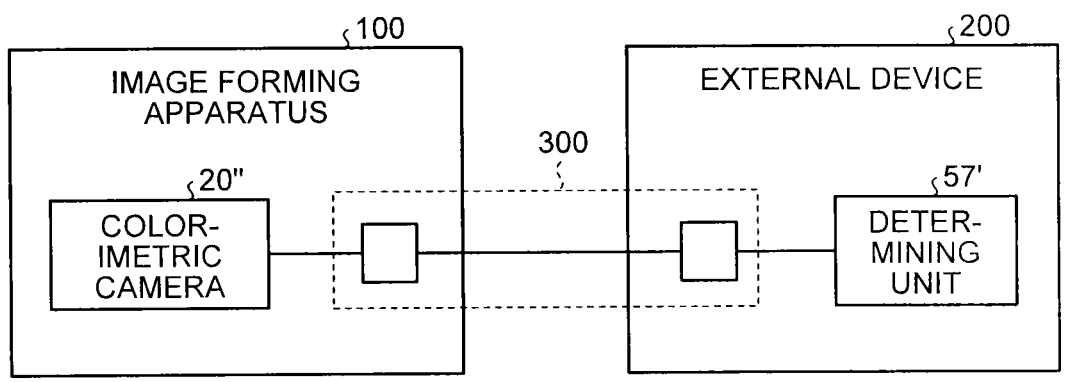
FIG. 15 is a diagram illustrating an example in which an external device has the function of a determining unit.

FIG. 15 is a diagram illustrating an example in which an external device has the function of the determining unit 57. The configuration illustrated in FIG. 15 includes an image forming system that includes the image forming apparatus 100 connected to an external device 200 in a manner of being capable of communicating with each other. The external device 200 is configured to perform the function of the determining unit 57 to thus determine whether or not the covering member 31 of the colorimetric camera 20 (or the optical path length changing member 409 of the colorimetric camera 400) is contaminated. Specifically, the image forming system includes a colorimetric camera 20" (having the configuration of the above-described colorimetric camera 20 (or the colorimetric camera 400) less the determining unit 57) of the image forming apparatus 100, a determining unit 57' of the external device 200, and a communication unit 300 that connects the colorimetric camera 20" to the determining unit 57' (the image forming apparatus 100 to the external device 200). A computer called a digital front end (DFE), for example, may be used for the external device 200. For the communication unit 300, wired or wireless P2P communication, communication using a network, such as a LAN and the Internet, and the like may be used.

Fifth Modification

The embodiment described above has been exemplified by the image forming apparatus 100 configured as a serial-head ink jet printer; however, the present invention is not limited thereto and is effectively applicable to various types of image forming apparatuses. To apply the present invention to an ink jet printer incorporating a line head system, a plurality of colorimetric cameras 20 (or colorimetric cameras 400) may be arrayed in a direction orthogonal to a conveying direction of the recording medium M. Alternatively, to apply the present invention to an electrophotographic image forming apparatus, the colorimetric cameras 20 (or colorimetric cameras 400) may be arrayed in the direction orthogonal to the conveying direction of the recording medium M at any position along the conveying direction of the recording medium M at least after fixing. When the colorimetry is performed for the colorimetric patterns (to acquire the RGB values) using the colorimetric cameras 20 (or colorimetric cameras 400) while the recording medium M is being conveyed, in particular, the colorimetric patterns are preferably formed into a patch that is long in the conveying direction of the recording medium M.

Figure 16:
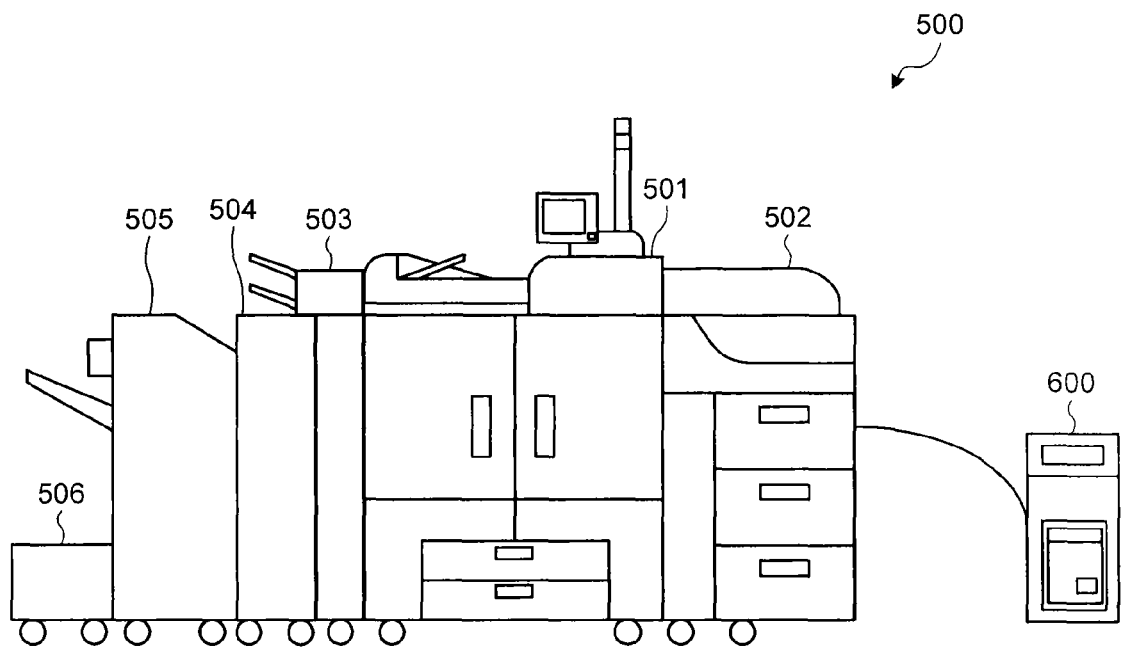
FIG. 16 is a diagram illustrating an appearance of an electrophotographic image forming apparatus configured as a production printer.

FIG. 16 is a diagram illustrating an appearance of an electrophotographic image forming apparatus 500 configured as a production printer. The image forming apparatus 500 illustrated in FIG. 16 includes a main unit 501 (an image recording unit) that uses toner as a coloring material to record an image on the recording medium M through an electrophotographic process. The image forming apparatus 500 further includes peripheral machines that may be combined with the main unit 501 to achieve their respective purposes, including a large-capacity paper feeding unit 502 that feeds paper, an inserter 503 to be used for supplying a cover or the like, a folding unit 504 that folds the recording medium M on which an image has been recorded, a finisher 505 that performs stapling, punching, or the like, and a cutter 506 that performs cutting. The image forming apparatus 500 is further connected to an external controller 600 called a digital front end (DFE).

Figure 17:
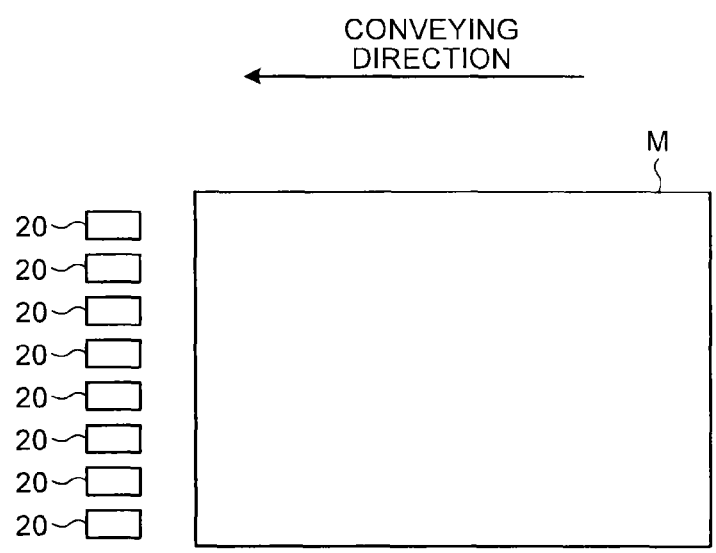
FIG. 17 is a diagram illustrating an exemplary disposition of colorimetric cameras in the electrophotographic image forming apparatus.

The electrophotographic image forming apparatus 500 configured as described above includes a plurality of colorimetric cameras 20 (or colorimetric cameras 400) arrayed in the direction orthogonal to the conveying direction of the recording medium M at a position on, for example, a path inside the finisher 505 along which the recording medium M is conveyed. FIG. 17 illustrates an exemplary disposition of the colorimetric cameras 20 in the electrophotographic image forming apparatus 500. FIG. 17 illustrates eight colorimetric cameras 20 arrayed in the direction orthogonal to the conveying direction of the recording medium M.

When the main unit 501 conveys the recording medium M on which the colorimetric patterns are recorded, for example, the colorimetric cameras 20 acquire the RGB values of the colorimetric patterns by causing the two-dimensional image sensor 25 to perform imaging at timing at which the colorimetric patterns arrive at a position opposed to the opening 24 in the housing 23. The colorimetric cameras 20 transmit to the main unit 501 the RGB values of the patch acquired through the imaging by the two-dimensional image sensor 25 or the colorimetric value of the patch calculated from the RGB values. Using the RGB values of the patch or the colorimetric value of the patch transmitted from the colorimetric cameras 20, the main unit 501 performs adjustments of the amount of toner to be stuck to the recording medium M (color adjustment). If the main unit 501 is configured such that the recording medium M after the fixing is sufficiently cooled inside the main unit 501, the colorimetric cameras 20 (or colorimetric cameras 400) may be arrayed in the direction orthogonal to the conveying direction of the recording medium M at a position along the conveying path inside the main unit 501 along which the cooled recording medium M is conveyed.

Others

While a specific embodiment and modifications thereof according to the present invention have been described in detail above, the present invention is not limited thereto and various further modifications and changes can be made when carrying out the invention without departing from the spirit of the invention. For example, the embodiment and the modifications described above are configured so as to inspect the covering member 31 or the optical path length changing member 409, whichever is applicable, for contamination. When the colorimetric camera 20 or the colorimetric camera 400 includes an optical member different from the covering member 31 or the optical path length changing member 409, however, the present invention can still be effectively applied to the inspection of the optical member for contamination. Additionally, the present invention can be widely applied to various types of imaging devices having similar mechanical configurations, in addition to the colorimetric camera 20 or the colorimetric camera 400 having the function of performing colorimetry for the colorimetric patterns.

The present invention has an advantageous effect in that an optical member disposed between a two-dimensional image sensor and an opening in a housing can be conveniently inspected for contamination.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An imaging device comprising:
   a housing having an opening in a surface thereof facing a subject;
   a light source that irradiates the subject with light;
   a two-dimensional image sensor that captures, from inside of the housing through the opening, an image of the subject illuminated by the light source;
   an optical member that is disposed between the two-dimensional image sensor and the opening, that protects the inside of the housing from outside, and that transmits light reflected off the subject; and
   a contamination inspection member that is disposed at a position outside an optical path of the light that is reflected off the subject and is incident upon the two-dimensional sensor, the position being between the opening and the optical member, and that provides inspection light for inspecting contamination on the optical member to be incident upon the two-dimensional image sensor via the optical member.

2. The imaging device according to claim 1, further comprising:
   circuitry configured to determine whether or not the optical member is contaminated using an inspection image obtained through imaging of the inspection light by the two-dimensional image sensor.

3. The imaging device according to claim 1, wherein the contamination inspection member is disposed on an inner wall of the housing between the opening and the optical member.

4. The imaging device according to claim 1, wherein the contamination inspection member is a reflecting member that provides reflected light from the light source to be incident upon the two-dimensional image sensor as the inspection light.

5. The imaging device according to claim 1, wherein the contamination inspection member is an inspection light source that irradiates the optical member with light and provides the light that has transmitted the optical member to be incident upon the two-dimensional image sensor as the inspection light.

6. The imaging device according to claim 5, wherein the inspection light source includes an intensity controller that changes intensity of the light irradiating the optical member.

7. The imaging device according to claim 5, wherein the inspection light source irradiates the optical member with light and provides the light that has transmitted the optical member to be incident upon the two-dimensional image sensor as the inspection light while the two-dimensional image sensor is moving relative to the subject.

8. An image forming apparatus comprising the imaging device according to claim 1.

9. The imaging device according to claim 1, further comprising:
   a reference chart; and
   a reflecting mirror that is inclined at a predetermined angle with respect to the surface of the housing and that guides an optical image of the reference chart onto the two-dimensional image sensor.

10. The imaging device according to claim 9, wherein the reflecting mirror is pushed against a cushioning member at the predetermined angle.

11. The imaging device according to claim 1, wherein the optical member is disposed substantially parallel to the opening.

12. A contamination inspection method executed by an imaging device that comprises:
    a housing having an opening in a surface thereof facing a subject;
    a light source that irradiates the subject with light;
    a two-dimensional image sensor that captures, from inside of the housing through the opening, an image of the subject illuminated by the light source; and
    an optical member that is disposed between the two-dimensional image sensor and the opening, that protects the inside of the housing from outside, and that transmits light reflected off the subject, the contamination inspection method comprising:
    providing, by a contamination inspection member disposed at a position outside an optical path of the light that is reflected off the subject and is incident upon the two-dimensional sensor, the position being between the opening and the optical member, inspection light for inspecting contamination on the optical member to be incident upon the two-dimensional image sensor via the optical member;

imaging, by the two-dimensional image sensor, the inspection light; and determining, by circuitry, whether or not the optical member is contaminated using an inspection image obtained through the imaging of the inspection light by the two-dimensional image sensor.

* * * * *